(12) United States Patent
Laurie et al.

(10) Patent No.: US 7,320,870 B2
(45) Date of Patent: Jan. 22, 2008

(54) OCULAR TEAR GROWTH FACTOR-LIKE PROTEIN

(75) Inventors: Gordon W. Laurie, Charlottesville, VA (US); Sandhya Sanghi, Temple, TX (US); Kumar Rajesh, Temple, TX (US); Angela J. Lumsden, Mosman Park (AU)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 11/714,586

(22) Filed: Mar. 6, 2007

(65) Prior Publication Data

US 2007/0167372 A1    Jul. 19, 2007

Related U.S. Application Data

(62) Division of application No. 10/468,372, filed as application No. PCT/US02/04971 on Feb. 20, 2002.

(60) Provisional application No. 60/269,900, filed on Feb. 20, 2001.

(51) Int. Cl.
G01N 33/53 (2006.01)

(52) U.S. Cl. ........................ 435/7.1; 435/7.2; 435/69.1; 435/70.1; 530/350; 436/501

(58) Field of Classification Search ............... None
See application file for complete search history.

(56) References Cited

U.S. PATENT DOCUMENTS

2002/0101604 A1   8/2002   Milne et al.
2002/0164669 A1   11/2002  Rueben et al.

FOREIGN PATENT DOCUMENTS

WO   WO 98/27205 A2   6/1998
WO   WO 98/35229 A1   8/1998

OTHER PUBLICATIONS

Rudinger, In *Peptide Hormones*, J. R. Parsons, ed., University Park Press, Baltimore, pp. 1-7, 1976.*
Lumsden, A.J., Dickinson, D.P., and Laurie, G.W., (1998). "Paired oligonucleotide screening for 'BM 180' in a human lacrimal gland cDNA library: Clome HL-2"., Am. Society for Cell Biology Annual Meeting.
Sanghi, S., and Laurie, G.W., (1999). "cDNA Cloning and Expression of 'lacritin', a novel secreted glycoprotein of the lacrimal gland"., Am. Society for Cell Biology Annual Meeting.
Sanghi, S., Kumar, R. Walton, S., and Laurie, G.W., (2000). "Quantitation of rat lacrimal secretion: novel sandwich ELISA with high sensitivity"., Exp. Eye Res., p. 651-658.
Rudinger, J., ""Characteristics of the amino acids as components of a peptide hormone sequence"," Peptide Hormones, University Park Press (Baltimore), (June 14, 1976).

* cited by examiner

*Primary Examiner*—Christina Chan
*Assistant Examiner*—Stephen Gucker
(74) *Attorney, Agent, or Firm*—Rodney L. Sparks

(57) ABSTRACT

The present invention relates to a novel lacrimal gland protein (designated lacritin) and the nucleic acid sequences encoding that protein. Lacritin has activity as a growth factor on both human corneal epithelial cells and on the lacrimal acinar cells that produce it. Accordingly, one embodiment of the present invention is directed to the use of lacritin to treat Dry Eye and other disorders requiring the wetting of the eye.

1 Claim, 3 Drawing Sheets

SEQUENCE LISTING

```
<160> NUMBER OF SEQ ID NOS: 15

<210> SEQ ID NO 1
<211> LENGTH: 12354
<212> TYPE: DNA
<213> ORGANISM: Homo sapiens
<220> FEATURE:
<221> NAME/KEY: exon
<222> LOCATION: (5194)..(5250)
<220> FEATURE:
<221> NAME/KEY: sig_peptide
<222> LOCATION: (5194)..(5250)
<220> FEATURE:
<221> NAME/KEY: exon
<222> LOCATION: (6801)..(6855)
<220> FEATURE:
<221> NAME/KEY: exon
<222> LOCATION: (7654)..(7794)
<220> FEATURE:
<221> NAME/KEY: exon
```

```
<222> LOCATION: (8196)..(8296)
<220> FEATURE:
<221> NAME/KEY: exon
<222> LOCATION: (9081)..(9143)

<400> SEQUENCE: 1
```

| | | | | | |
|---|---|---|---|---|---|
| acatttttaa | aatttttca | ctcattgctt | tgtctttaca | cctccccgat | ggccaaggtg | 60 |
| gaagatcgga | ggcatcacag | gagtgtggca | gagcttgtgc | aggccacagg | gcttggcaga | 120 |
| gaagacaagc | catgtcgagc | acagcagcca | gggtagaatg | gccctcggag | atcaacgtgt | 180 |
| gcctgtgtct | ccaatgcagg | agcagtctac | cctaaatagt | ccatgtcaat | tcctcccttt | 240 |
| ggagtctctg | cttccccacc | agcccccaga | acatggccta | acacacaggg | agggaatga | 300 |
| ggaaaagaca | ttcatcacag | ttcagacagg | aagtggtgta | tcagtggaga | ggtccaagta | 360 |
| gaaaacaaat | ggcacactca | ggagggctta | tatatatata | taaatacttt | aagttctagt | 420 |
| gtacatgtgc | acaatgtgca | ggtttgttac | atatgtatac | atgtgccgtg | ttggtttgct | 480 |
| gcacccatta | actcatcatt | taccttaggt | atttctccta | atgctatccc | tcccccatcc | 540 |
| ccccacccca | caacaggcct | cggtgtgtga | tgttccccac | cctgtgtcca | agtgttgtca | 600 |
| ttgttcaatt | cccacctatg | agtgagaaca | tgtggtgttt | ggttttctgt | ccttgcgata | 660 |
| gtttgctcag | aatgatggtt | tccagctta | tccatgtccc | tacaaaggac | atgaactcaa | 720 |
| ccttgtttat | ggctgcatag | tattccatgg | tgtatatgtg | ccacattttc | ttaacccagt | 780 |
| ctatcattga | tggacatttg | ggttggttcc | aagtctttac | tattgtgaat | agtgccacaa | 840 |
| taaacataca | tgtgcatgca | tctttatagt | agcatgattt | ataatccttt | gggtatatac | 900 |
| ctagtaatgg | gatctttggg | ttaaatggta | tttctagttc | tagatccttg | aggaatcgcc | 960 |
| acactgtctt | ccacaatggt | tgagctagtt | tacactccca | ccgatggtgt | aaaagcattc | 1020 |
| ctatttctcc | acatcctctc | cagcacctgt | tgtttcctga | cttttaatt | attgccattc | 1080 |
| taactactgt | gagatgatat | ctcattgtgg | ttttgatttg | catttctctg | atggccagtg | 1140 |
| atgatgagca | ttttttcatg | tgtctgctgg | ctgcataaat | ctcttctttt | caaaagtgtc | 1200 |
| tgtccatatc | ctttgcccac | tttttgatgg | ggttgtttga | ttttttcttg | taaatttgtt | 1260 |
| taagttcttt | gtagattctg | gatattagcc | ctttgtcaga | tgggtagatt | gcaaaaattt | 1320 |
| tctcccattc | tgtaggctgc | ctgttcactc | tgatggtagt | ttcttttgct | gtgcagaagc | 1380 |
| tctttagttt | aattagatcc | catttgtcta | ttttggcttt | tgttgccatt | gcttttggtg | 1440 |
| ttttagtcat | gaagtacttg | cccatgccta | tgtcctgaat | ggtattgccc | aggttttctt | 1500 |
| ctagggtttt | tatggtttta | ggtctaacat | ttaagtcttt | aatctatctt | gaattaattt | 1560 |
| ttgtataagg | tgtaaggaag | ggatccagtt | tcagctttct | acatatggct | agccagtttt | 1620 |
| cccagcacca | tttattaaat | aaggaatcct | ttccccattt | cttgttttg | tcaggtttgt | 1680 |
| caaagatcag | atggttgtag | atgtgtggtg | ttatttctga | ggcctctgtt | ctgttccatt | 1740 |
| ggtctatatc | tgttttggca | ccagtaccat | gctgttttgg | ttactgtaag | ctggtagtat | 1800 |
| agtttgaagt | caggtaatgt | gatgcctcca | gcttgttct | ttttgcttag | gattgtcttg | 1860 |
| gcaatgcagg | ccctttttg | gttccatatg | aactttaaag | tagttttttc | cacttctgtg | 1920 |
| aagaaagtca | ttggtagctt | gatggggatg | gcattgaatc | tctaaattac | cttgggcagt | 1980 |
| atggccattt | tcacgatatt | gattcttcct | atccaagagc | atggaatgtt | cttccatttg | 2040 |
| tttgtgtcct | cttatttcat | tgagcagtgg | tttgtggttc | tcaggagggc | ttttttaaa | 2100 |
| aaaggttctt | taaggaaaaa | tgtatctatt | atttacagag | attcaagtat | ggactagcaa | 2160 |

```
cagcaggaag tctgaagcag cgtgttgggg ggtgggggtg aataatgtca cctgacaaca    2220
agagatggcg ctctgaaaca gggaccagac agaagctgca gtcagagaga aacagccatt    2280
gccacaccat gctgcattaa gtatccgtgg ctgtaaaaat tattcaaaca tttggtggct    2340
tcacacatga tttcttatcc acagttgtta tggatcagca gtccaggtac agatgcgccc    2400
tcagacacag agtctctaat gaggctgcag tcaaggtatc atcgaggctg cggtcacctc    2460
aaaactcagc tgaggaaaga cccacttcca agctcagtca cgtggtagct ggcagggttg    2520
agttcctcac agatagctgg actaagggcc tcggctcctt actggctaca ggctggaggc    2580
tgtcctcggt ttcttgccac gtaggtctct ccacaggaca gcctcacaca tggccactca    2640
cttcatcaga gcaagctgag aagatccaga cagagtgt gtgtaaacaa gactaaagtc    2700
atagtctcag aactgactac ctcatcactt tgccatcttc tatttgttag gagtgaatct    2760
cgagacccag cccagttaag cagaggaaat tacagcaggg caccaatgcc aagacgtagg    2820
catcaccagg agctatctct gaagtcgtcc taccacacat gccaaagcaa gagagggagc    2880
aggaggaaca aatgccttga tctctccctt ttcccaccct cccatctccc acctgtgtct    2940
cccattggcc aaactcaact cgaagctaga gggcatggga gcccaggtga tacagcccat    3000
agaggcatcc ttccagacca gtgcagagat gagagagaat aaacctgagg cagaggggag    3060
agaggtacaa cgagcagccc atgagacaag acacagatca gcgaactgac agtcatcatg    3120
gaggtcagat aacctagaaa acaagacatc acacagagca gcccctcacc catatccatg    3180
aggtccgtca agacattgca cagagcagcc tctcacccat atccatgagg tctgcctctt    3240
taatctatgc acccaattct ttcccaggct ctataatttg gggtaacatt tctctgggcc    3300
ctgttataga ataatgaaaa ttttctataa aacaaatgtc cttactttca cctcatccct    3360
atttatgtaa atgcttgcct ctttaattac tgaggccagg aggaagattt gggagaggaa    3420
agggctatgc ggtgacattt ggaaagaccc tgctctgtga cagttctagt gttgacgcca    3480
aagttctcat ttcctcttag aaaagtcttg tgcaaatagc ataatttgct cctgttgact    3540
tttttaatgt gctcatggag actgctcggg atctagatct gtttgggatc tgcaggactt    3600
ctccttctgc agtgtacaca cacgtgcaca cacgtatgtg cacataccca gggcactggt    3660
gccatcaaaa cttctctctt g ttcttcagcc ttccccattc caggtaaggc caccaccacc    3720
ttcaaggctc ccaggcccag accctcaggc aggtagcaat tgccaaggct ttaatgtccc    3780
accccattaa ttttatcttc ctttatctcc tgaaaagatt aatgttctaa accctggcac    3840
ccaaaacacc ctcatgttga aaactcttca ataccccctt ctcacactca tcttcagagc    3900
taccatgagg cagagaagcc tccggaatca gcccacatgg ggctgggtga atgccaacac    3960
caagcaaggg gaaagtcaca aattgacatc cagcaccttaa ttctccaccc ttcagcccct    4020
caactgactc ctgctccacg gcccgttcta ttaatatcta gcatttagca ccagcctgga    4080
caaaaaccta cttggaaaga tggtacaaga accccacaca actccataga acttcgctgt    4140
ctaaaaaaat gctttgccgt atattatccc acttaatctc caccactatg ctgtacatag    4200
gagccacaac tcctagacaa caaataaaaa tcctatcact tttcaaatcc taacattttc    4260
atatgacaaa gccagaactc aaaatccaga cctctagagt cccagatcag gaaaggaaga    4320
aacgccaagt caaagagaag cttctttaga ataatctgct tttctggatt attcacacca    4380
tgggtcagct ccccacttga agtcagaacc aagctccaat ttcagtgaac caccatcatg    4440
ctttgaccag gagattctct cagaaatgtg gggtcccatt gagtaggcct gaagacagag    4500
attgacaggc ctatgtgagc ctggaggagt tctttttagg ggctggataa tgtcaagaac    4560
```

```
agagaacaac tccagagaag gcacacacgc cttcaaaccc atcccctcat ggggagaaag    4620
cagccaggaa ctcaggcctc aagtgttcta ggtgtggtct cccaaggaaa cgggctcact    4680
tagtttgggg aaaccttcaa accctgcact gagtcctatg tagactggga cagaaggtgg    4740
acaatgtaat cccctgagcc ctcaacctcc tcctggagag atgacaagat taagatttct    4800
ctaccagaac cctcaacaga cacatcccag aatctcccca agtgaaatgt gctctaccta    4860
ccgtccctga gagcccaggg gtgtgaaccc agagggcagg tgtggtgggg aagggaggag    4920
ggagaaagaa aagggatggc tgggagttag agaaaggctc ctatccagga cctgcctgca    4980
aggatcccag gtatcagcca gcccaaccta gcccttgttg acttagcagg tgacagtttg    5040
gggaagaagg ggaggaggat gcggaagtca cacctctcca ggcttggttc ccattggccc    5100
ttgatatcct taaaagggcc cagcaatttc agcatcctta ttccccagac cttctgcaga    5160
ttctgtggtt atactcactc ctcatcccaa aga atg aaa ttt acc act ctc ctc    5214
                                 Met Lys Phe Thr Thr Leu Leu
                                  1               5 ttc ttg gca gct gta gca ggg gcc ctg gtc tat gct ggtgagtatg           5260
Phe Leu Ala Ala Val Ala Gly Ala Leu Val Tyr Ala
    10                  15 gcctttcctc tgcgcccac aagagtcctc ccagtccaag gagcccctca ctcctgcctt    5320
cacccctctc ctcctctctc agtgctattc tggtttccct gcctctgcaa gtgactcctc    5380
tcccagttct ccacacgtgg cctctgcacc ccactggcca gaggaaccca gaactctctg    5440
gcctctgcct gccctcccag ctcatctcct cacacaccat tgtttaccca ctatgcctca    5500
gctacactgg cttctctggt gtcccctgca tgtagttgag cagggtgtcc cctacacgag    5560
ggtgcccagg caaggagtgg tagaagctaa aatctggccg acactctact tgccaagcag    5620
tgagcctggc ccctggctgt gtctcttagg aggaagggat gcctttttt ttttttttt     5680 tttgagaccg agtctccctc tgttgcccag gctggagtgc agtggcacga tctctgctca    5740
ctgcaacatc cacctcctgg gttccagcga ttatcttgcc tcagcctcct gggtagctgg    5800
gactacaggc tcatgccacc ttgcccagct aattttgtat ttttagtaga cggtgtttt    5860 caccatgttg gccaggttgg tctcgaactc ctgacctcag gtgatccgac tgccttggcc    5920
tcccaaagtg ttggaattac aggcgtgagc caccgtgccc tgctgggatg cctttttga    5980 tccacagaag cactatttgg gccatgatga tcctgctgtt ccttgaacat caggatcttc    6040
cttcttgtcc tttcctcgtc tagaatgctt tccctctccc tggcccttc ccccaaccaa    6100 ctctaatgtc acctggccaa tgatttttca tctagaaaat ctcagtttac atataattcc    6160
ccaaaaaggc cttccatgca catgcggaac aaatcagatc catgtgccct tctcgcacca    6220
ggctgcacgt tcccttccag cactgtcaca ccagccatta ataatttcg taaaaggaca    6280 gatgtaagct ctgtcaggc aggggtcttg tctgccctct tcagcactgc acctccatct    6340
cttggcacag agctttgcat aaatgttgtg ttgaaagaat aaagggaatc aaggctgggg    6400
tctcaatcct gcaaatcgct caaatatggc cccataaccc ccacatactg tcctcctcca    6460
ccacagagga ggttgagccc ctctgaccat ggccagctcc atgacagaca cctcagggaa    6520
gcctaccaag ccaggggcca gtcaggagga aggcactgtt ccaagagaca ttacacttct    6580
cagaggggaa gttatttcaa aagccacagg agttaaacat cagagagtgc cccagtagac    6640
ccgctgatat ggtggaaggg catgtccaac ccaaagggaa attgatcccc ttctatccat    6700
gagcattccc aggagataag ctttgggaat gggaggggag ggtggctcga gtaggtccgg    6760
```

-continued

```
ttcggtcctt gctctcatct ggcatgtttc ccccattgca gaa gat gcc tcc tct    6815
                                             Glu Asp Ala Ser Ser
                                                  20 gac tcg acg ggt gct gat cct gcc cag gaa gct ggg acc t gtgagtcctc   6865
Asp Ser Thr Gly Ala Asp Pro Ala Gln Glu Ala Gly Thr
 25              30                  35 ctctccctgc tgccctagcc ctcgttggga aggtttaaca gttagggatg tgagtggtgg   6925
ctgggagaag aagccagtgg gaggagatct ggattctgtg cttggtggta atggggaggg   6985
gcaggtaata taataaagaa ggtggcatgg gttgaaatgg tacaaggcta aggacaaaag   7045
aggatgaccc agagaggcaa ggacaatagg gagcatgggg aaaaggttat tgtgaataaa   7105
agggagagaa acatgaggtt aagtggtaag ggcaatgtct cacatggcat taataccttc   7165
acctgcaaac acctcccatt actcccaatt ccttagcaag ataaccatta tctggcctct   7225
aacctcattt tccaaccccca ttttccatga ctctctttta tgtcgcaccc ccatcagcta   7285
aattgaactt gtttccattc cccacacatg ccttcgcctg acctcttact cactgcctgc   7345
ccccagggaa gccctttgg tacatcctct cctgctaaca tcctgccttc aagatccagc   7405
ttctctatga agtgctcccc gattctcacc atccctagt ccaaatcctt ccccaaccct   7465
gcccgctgca ttccaagaga cacacagcat gcagaaatgc tatctccctt aagggggcag   7525
cgtttaagcc atatcacttc tgtatcctgg cacccagcac acattaggta tcctggggcc   7585
ctgcaaccca ttccaaaaga aacaaacact ttcactttgc taaaatccat caatttgtgc   7645 attcacag ct  aag cct aat gaa gag atc tca ggt cca gca gaa cca gct    7694
            Ser Lys Pro Asn Glu Glu Ile Ser Gly Pro Ala Glu Pro Ala
                 40                  45                  50 tca ccc cca gag aca acc aca aca gcc cag gag act tcg gcg gca gca    7742
Ser Pro Pro Glu Thr Thr Thr Thr Ala Gln Glu Thr Ser Ala Ala Ala
         55                  60                  65 gtt cag ggg aca gcc aag gtc acc tca agc agg cag gaa cta aac ccc    7790
Val Gln Gly Thr Ala Lys Val Thr Ser Ser Arg Gln Glu Leu Asn Pro
     70                  75                  80 ctg a gtaagtctct gtctctatgc cagatcaaca acctagaaaa gtctctggct        7844
Leu gcaggcccac atcacacctc cacgcacaga gataagcctg gtgagaagca ggtagactca   7904
aacagctgaa cacaaaggca caaatgggat tgtgcattgc acccacacac aacgttttca   7964
caatagtaga tgttgcagcc tgcacaatac atggtttctg tcctggctca cacaacttcc   8024
tatgagagaa gtgctggagc cctcagcaaa acttctgcac tttaggactt tctgtaggga   8084
tgatgtcctg ggtggagtgg gggtggggggg cgggtgcagg tggggcaatg cagagttctc   8144
tttaaatgag gtgattttc tgctgatgtg attgttctgc tccaaaatta g aa tcc      8200
                                                         Lys Ser ata gtg gag aaa agt atc tta cta aca gaa caa gcc ctt gca aaa gca    8248
Ile Val Glu Lys Ser Ile Leu Leu Thr Glu Gln Ala Leu Ala Lys Ala
         90                  95                 100 gga aaa gga atg cac gga ggc gtg cca ggt gga aaa caa ttc atc gaa    8296
Gly Lys Gly Met His Gly Gly Val Pro Gly Gly Lys Gln Phe Ile Glu
     105                 110                 115 agtgagtgca tcccaaggca aggctttgtg ggaatgagaa tactcaccac ccaccatccg   8356
ggggtgggat atgggacaga acttgccccc atttccacct cacatatgag acttggaatt   8416
gccacagccc ctgctgttga agacccctca ctttgtgctt tcatatgttt ccaatttctc   8476
atccagattc aaaattgccag ctgggcacgg tggttcacgc ctgtaatccc agcactttgg   8536
gaggccaagg caggtggatc gcttgagccc aggagttcaa gactagcctg gcaacatgg    8596
```

```
cgatacccca tctctacaaa aaatacaaa aattagccag gcgtggtggc acatgcctgt    8656
agtcccagct acttgggagg ctaaggtggg aggatcacct gagcccgtga ggcagagatt    8716
gcagtgggcc gagattgtgc cactgcactc catcctgggt gacagagaaa gaccctgtct    8776
caaaaaaaaa gaacagattc aatgtgccat gttgtctgat attgattcac ctgggtcta     8836 acccccctacc ttcccgcagc agagcctgct tgtttctatt cttgtcccct gccctgcca    8896 aggtggggaa gagggtaggt ccttcaggct ctggtgaatc taatctcaat ccctccaact    8956
tctgtgtaag cctctccaga gtctcagtaa gtctggaaag cagagatgga attgaggaga    9016
aatggaaggg gtggagctgg tgcctggggt cctaaaagcc tcatttgtct catctttcct    9076 tcta gat gga agt gaa ttt gca caa aaa tta ctg aag aaa ttc agt cta     9125
     Asp Gly Ser Glu Phe Ala Gln Lys Leu Leu Lys Lys Phe Ser Leu
     120             125                 130 tta aaa cca tgg gca tga gaagctgaaa agaatgggat cattggactt               9173
Leu Lys Pro Trp Ala
    135 aaagccttaa ataccttgt agcccagagc tattaaaacg aaagcatcca acttgctgtg      9233 tgcctgtgct ctatgggatg ggccctggag gaagtgcagg gagaaaagcc ctccctggac     9293 caacacaagg cataggatgt cctgacccag gcccttggcc agtcacaggc tgcctggaag    9353 gcagagcctc taacaagccc ttttattcac ttggagccac atccacattg ctgagcctcc    9413 tttgagtcca aatgccactc cagttttcgt ccccctctta ctcttcacac attactccta   9473 gtgacatttg agcatttcca aaaattaaat caaattccaa agaaccagga tttatcatcc    9533 tgaaaataat caaagcctga gccatttata ctaaagccac tttctggtac ctttatcaga    9593 aattcatctc tcctgccctc tattcgtaca ttctacactg gccaaagtg gctggcaatg     9653 gctaattagg tcagacagta aagtaatgag ctactacagt gacaactggc acttggctaa    9713 gaagaccaat tgaatccatt aaggttattc ttgtgatgtg gtgcagagaa accacttttg    9773 actgtgctct agatgtgcaa attatcttcc ccaaaggact aaagtctctc aaagggtct     9833 tggtcacctc tttctcctcc tgcaactttg ttttcctccc ctacagctca tggctgtgtc    9893 ttgcacacac atgaaccagg gaagatcact catgacttca gggggcaaag aaagcagtca    9953 gatcttctgc cagaccctc cccaggccag gcacagggtc ttctgctctt taacatgccc     10013 ggagccattg attctagact gttcttccca ccccatctta gtttattttc tgttgctcat    10073 aacagaatat ctaaaactgg ataatttata agacgcaaaa tgtacttctt acagttctag    10133 agctaggaag tccaaggtca agggggcatg tctggcaaga gctttcttgc tggcagggaa    10193 tctctgcagg atcccaagct ggaatagaga atcacatagt gaggtggctg tccacgctag    10253 ctcagctctc ttcctcttct tagaaagcct ccagtctcac tcctgtggca aaccattaat    10313 ccattaaccc attaattcat taatccatag atggattaat ctattcacaa gggcaaagac    10373 ctcatgaccc aatcatttct ttttcttttt gttttttaag acagagtcct gttctgtcgc    10433 ccacactgga gttcaacggc tcaatctcgg ctcactgcaa cctctgcctc ccgggttcaa    10493 gcaattctcc tgcctcagcc tcccaagcag ctaggattac aggtgcccac cgccacacct    10553 ggctaatttg ttgtattttt agtagagacg gggtttcacc atgttggcca ggatggtctc    10613 aaactcctga cctcatatga tccacctgcc taggcctccc aaagtgctga gattacagac    10673 atgagccact gcgcccagca tgaaccaatc atttcttaat aaccctgcct ttcaatattg    10733 ttactttagg gattaagttt caatgtaagt tttggagggg acaaacactc aaactatacc    10793
```

-continued

| | |
|---|---:|
| attctactcc tggccctctg aaactcatgt ccttctcaaa tataaatata ttcattccaa | 10853 |
| ctccatagcc ccaaaatctt agctcattcc agcaccaact caaaagtcca aagtccagag | 10913 |
| tatcatctgt gagcctgtga aatacaaacg agttatctac ttttaagata cagttgtggt | 10973 |
| aaaagcataa aacagacatt cccattccaa aatggaggaa tagacaaaaa gaaacgagta | 11033 |
| acaggtctca agcaaatctg aaacccagca gggcagacat taaatcttaa agctgaagaa | 11093 |
| taatttcttt tgactctgtg tgtggcctcc catcccacaac ggggtatggg ttaggccccc | 11153 |
| aagacttcag gcagcctcac ccttatggct ttgctcagtg cagcccatgt gactgctcct | 11213 |
| aggtattgga gtctggtgcc tgaagctttc ccaggtgggt gttgcatact gccagtgact | 11273 |
| gcacacttct gggttcccag tagtggtccc actcccacag ctctactagg cattaccta | 11333 |
| atggagactc tctacggtgg caccacttcc atggctctgc tagatgggga ctctttgcag | 11393 |
| tggctctgcc cctgtgacaa atctttgcct gggctcctag gcttttgatg atatccttg | 11453 |
| aaatcttggt ggaggctgcc aagctgccac agcttttgct gtctgcaagc ctgcagagtc | 11513 |
| agcaccacct ggacactgcc aaggtttatg gcttctacct tccaaaactg cagcacaagc | 11573 |
| tacaattggg gtcacttgag ccttggctag ggcagccatg aagctctgca ctggggtttc | 11633 |
| agggcagagt cccaaggcac cattctgccc ttctagacct ctgggcctat aacaggaggg | 11693 |
| gcaccctcaa agatctctga aatgcatttc aggtctttct tcatcgtctt gagaaatagc | 11753 |
| atccggctcc cttctatctg tgctaatctt tttagctgca cccttgatct cctcttctga | 11813 |
| atgtgctttt tcactcttca tgtggccagg ctgacagttt tccaactctt tccactctgc | 11873 |
| ttccagttta atgtaaattt tctttatctt tataattgtc tttgaattat tcctttgctc | 11933 |
| ccaaatctca gcataagtgg ccaaaagtaa ccatgcacct ccttctatat tttgcttaga | 11993 |
| aatttcttct gcagatactc tagttcgtca ctctcaagtt tggccttcca caaagccctt | 12053 |
| aaatgtagac acagttcagt caagttctct gtcaatttat aacaaggatg gtctttactc | 12113 |
| cagtttccaa taccttattc ctcagttcca tctgaaatct catcagaatg gccttactgt | 12173 |
| tcatatttca actagcattc tggtcacaat cacttaacaa atctctaaga agttccaaac | 12233 |
| tttccaaaga actgaggtgc tccatgagtt ctccacccct gcagcaaact tctgcctgga | 12293 |
| catctaggtg ttttcataca tcctctgaaa tctaggtgga ggttcccaaa ccccaattct | 12353 |
| t | 12354 |

<210> SEQ ID NO 2
<211> LENGTH: 522
<212> TYPE: DNA
<213> ORGANISM: Homo sapiens

<400> SEQUENCE: 2

| | |
|---|---:|
| gaattcgcgg ccgcgcagat tctgtggtta tactcactcc tcatcccaaa gaatgaaatt | 60 |
| taccactctc ctcttcttgg cagctgtagc aggggccctg gtctatgctg aagatgcctc | 120 |
| ctctgactcg acgggtgctg atcctgccca ggaagctggg acctctaagc ctaatgaaga | 180 |
| gatctcaggt ccagcagaac cagcttcacc cccagagaca accacaacag cccaggagac | 240 |
| ttcggcggca gcagttcagg ggacagccaa ggtcacctca agcaggcagg aactaaaccc | 300 |
| cctgaaatcc atagtggaga aaagtatctt actaacagaa caagcccttg caaaagcagg | 360 |
| aaaaggaatg cacggaggcg tgccaggtgg aaaacaattc atcgaaaatg gaagtgaatt | 420 |
| tgcacaaaaa ttactgaaga aattcagtct attaaaacca tgggcatgag aagctgaaaa | 480 |
| gaatgggatc attggactta aagccttaaa taccccttgta gc | 522 |

<210> SEQ ID NO 3
<211> LENGTH: 416
<212> TYPE: DNA
<213> ORGANISM: Homo sapiens

<400> SEQUENCE: 3

```
tgaaatttac cactctcctc ttcttggcag ctgtagcagg ggccctggtc tatgctgaag      60
atgcctcctc tgactcgacg ggtgctgatc ctgcccagga agctgggacc tctaagccta     120
atgaagagat ctcaggtcca gcagaaccag cttcaccccc agagacaacc acaacagccc     180
aggagacttc ggcggcagca gttcagggga cagccaaggt cacctcaagc aggcaggaac     240
taaaccccct gaaatccata gtggagaaaa gtatcttact aacagaacaa gcccttgcaa     300
aagcaggaaa aggaatgcac ggaggcgtgc caggtggaaa acaattcatc gaaaatggaa     360
gtgaatttgc acaaaaatta ctgaagaaat tcagtctatt aaaaccatgg gcatga        416
```

<210> SEQ ID NO 4
<211> LENGTH: 138
<212> TYPE: PRT
<213> ORGANISM: Homo sapiens

<400> SEQUENCE: 4

```
Met Lys Phe Thr Thr Leu Leu Phe Leu Ala Ala Val Ala Gly Ala Leu
1               5                   10                  15

Val Tyr Ala Glu Asp Ala Ser Ser Asp Ser Thr Gly Ala Asp Pro Ala
            20                  25                  30

Gln Glu Ala Gly Thr Ser Lys Pro Asn Glu Glu Ile Ser Gly Pro Ala
        35                  40                  45

Glu Pro Ala Ser Pro Pro Glu Thr Thr Thr Thr Ala Gln Glu Thr Ser
    50                  55                  60

Ala Ala Ala Val Gln Gly Thr Ala Lys Val Thr Ser Ser Arg Gln Glu
65                  70                  75                  80

Leu Asn Pro Leu Lys Ser Ile Val Glu Lys Ser Ile Leu Leu Thr Glu
                85                  90                  95

Gln Ala Leu Ala Lys Ala Gly Lys Gly Met His Gly Gly Val Pro Gly
            100                 105                 110

Gly Lys Gln Phe Ile Glu Asn Gly Ser Glu Phe Ala Gln Lys Leu Leu
        115                 120                 125

Lys Lys Phe Ser Leu Leu Lys Pro Trp Ala
    130                 135
```

<210> SEQ ID NO 5
<211> LENGTH: 5193
<212> TYPE: DNA
<213> ORGANISM: Homo sapiens

<400> SEQUENCE: 5

```
acatttttaa aattttttca ctcattgctt tgtctttaca cctccccgat ggccaaggtg      60
gaagatcgga ggcatcacag gagtgtggca gagcttgtgc aggccacagg gcttggcaga     120
gaagacaagc catgtcgagc acagcagcca gggtagaatg ccctcggag  atcaacgtgt     180
gcctgtgtct ccaatgcagg agcagtctac cctaaatagt ccatgtcaat tcctcccttt     240
ggagtctctg cttcccccacc agcccccaga acatggccta acacacaggg aggggaatga     300
ggaaaagaca ttcatcacag ttcagacagg aagtggtgta tcagtggaga ggtccaagta     360
gaaaacaaat ggcacactca ggagggctta tatatatata taaatacttt aagttctagt     420
```

-continued

```
gtacatgtgc acaatgtgca ggtttgttac atatgtatac atgtgccgtg ttggtttgct      480
gcacccatta actcatcatt taccttaggt atttctccta atgctatccc tcccccatcc      540
ccccacccca caacaggcct cggtgtgtga tgttccccac cctgtgtcca agtgttgtca      600
ttgttcaatt cccacctatg agtgagaaca tgtggtgttt ggttttctgt ccttgcgata      660
gtttgctcag aatgatggtt tccagctttta tccatgtccc tacaaaggac atgaactcaa      720
ccttgtttat ggctgcatag tattccatgg tgtatatgtg ccacattttc ttaacccagt      780
ctatcattga tggacatttg ggttggttcc aagtctttac tattgtgaat agtgccacaa      840
taaacataca tgtgcatgca tctttatagt agcatgattt ataatccttt gggtatatac      900
ctagtaatgg gatctttggg ttaaatggta tttctagttc tagatccttg aggaatcgcc      960
acactgtctt ccacaatggt tgagctagtt tacactccca ccgatggtgt aaaagcattc     1020
ctatttctcc acatcctctc cagcaccgt tgtttcctga cttttaatt attgccattc       1080 taactactgt gagatgatat ctcattgtgg ttttgatttg catttctctg atggccagtg     1140
atgatgagca tttttttcatg tgtctgctgg ctgcataaat ctcttctttt caaaagtgtc    1200
tgtccatatc ctttgcccac ttttttgatgg ggttgtttga tttttttcttg taaatttgtt   1260 taagttcttt gtagattctg gatattagcc ctttgtcaga tgggtagatt gcaaaaattt     1320
tctcccattc tgtaggctgc ctgttcactc tgatggtagt ttcttttgct gtgcagaagc     1380
tctttagttt aattagatcc catttgtcta ttttggcttt tgttgccatt gcttttggtg     1440
ttttagtcat gaagtacttg cccatgccta tgtcctgaat ggtattgccc aggttttctt     1500
ctagggtttt tatggttta ggtctaacat ttaagtcttt aatctatctt gaattaattt      1560
ttgtataagg tgtaaggaag ggatccagtt tcagctttct acatatggct agccagtttt     1620
cccagcacca tttattaaat aaggaatcct ttccccattt cttgttttg tcaggtttgt      1680 caaagatcag atggttgtag atgtgtggtg ttatttctga ggcctctgtt ctgttccatt     1740
ggtctatatc tgttttggca ccagtaccat gctgttttgg ttactgtaag ctggtagtat     1800
agtttgaagt caggtaatgt gatgcctcca gctttgttct ttttgcttag gattgtcttg     1860
gcaatgcagg cccttttttg gttccatatg aactttaaag tagtttttc cacttctgtg     1920 aagaaagtca ttggtagctt gatggggatg cattgaatc tctaaattac cttgggcagt     1980
atggccattt tcacgatatt gattcttcct atccaagagc atggaatgtt cttccatttg    2040
tttgtgtcct cttatttcat tgagcagtgg tttgtggttc tcaggagggc ttttttttaaa   2100 aaaggttctt taaggaaaaa tgtatctatt atttacagag attcaagtat ggactagcaa    2160
cagcaggaag tctgaagcag cgtgttgggg ggtggggtg aataatgtca cctgacaaca      2220
agagatggcg ctctgaaaca gggaccagac agaagctgca gtcagagaga aacagccatt    2280
gccacaccat gctgcattaa gtatccgtgg ctgtaaaaat tattcaaaca tttggtggct    2340
tcacacatga tttcttatcc acagttgtta tggatcagca gtccaggtac agatgcgccc    2400
tcagacacag agtctctaat gaggctgcag tcaaggtatc atcgaggctg cggtcacctc    2460
aaaactcagc tgaggaaaga cccacttcca agctcagtca cgtggtagct ggcagggttg    2520
agttcctcac agatagctgg actaagggcc tcggctcctt actggctaca ggctggaggc    2580
tgtcctcggt ttcttgccac gtaggtctct ccacaggaca gcctcacaca tggccactca    2640
cttcatcaga gcaagctgag aagatccaga gacagagtgt gtgtaaacaa gactaaagtc    2700
atagtctcag aactgactac ctcatcactt tgccatcttc tatttgttag gagtgaatct    2760
```

```
cgagacccag cccagttaag cagaggaaat tacagcaggg caccaatgcc aagacgtagg    2820
catcaccagg agctatctct gaagtcgtcc taccacacat gccaaagcaa gagagggagc    2880
aggaggaaca aatgccttga tctctcccct tccccaccct cccatctccc acctgtgtct    2940
cccattggcc aaactcaact cgaagctaga gggcatggga gcccaggtga tacagcccat    3000
agaggcatcc ttccagacca gtgcagagat gagagagaat aaacctgagg cagaggggag    3060
agaggtacaa cgagcagccc atgagacaag acacagatca gcgaactgac agtcatcatg    3120
gaggtcagat aacctagaaa acaagacatc acacagagca gcccctcacc catatccatg    3180
aggtccgtca agacattgca cagagcagcc tctcacccat atccatgagg tctgcctctt    3240
taatctatgc acccaattct ttcccaggct ctataatttg gggtaacatt tctctgggcc    3300
ctgttataga ataatgaaaa ttttctataa acaaatgtc cttactttca cctcatccct    3360
atttatgtaa atgcttgcct ctttaattac tgaggccagg aggaagattt gggagaggaa    3420
agggctatgc ggtgacattt ggaaagaccc tgctctgtga cagttctagt gttgacgcca    3480
aagttctcat ttcctcttag aaaagtcttg tgcaaatagc ataatttgct cctgttgact    3540
tttttaatgt gctcatggag actgctcggg atctagatct gtttgggatc tgcaggactt    3600
ctccttctgc agtgtacaca cacgtgcaca cacgtatgtg cacataccca gggcactggt    3660
gccatcaaaa ctttctcttg ttcttcagcc ttccccattc caggtaaggc caccaccacc    3720
ttcaaggctc ccaggcccag accctcaggc aggtagcaat tgccaaggct ttaatgtccc    3780
accccattaa ttttatcttc ctttatctcc tgaaaagatt aatgttctaa accctggcac    3840
ccaaaacacc ctcatgttga aaactcttca atacccctt ctcacactca tcttcagagc    3900
taccatgagg cagagaagcc tccggaatca gcccacatgg ggctgggtga atgccaacac    3960
caagcaaggg gaaagtcaca aattgacatc cagcaccta ttctccaccc ttcagcccct    4020
caactgactc ctgctccacg gcccgttcta ttaatatcta gcatttagca ccagcctgga    4080
caaaaaccta cttggaaaga tggtacaaga accccacaca actccataga acttcgctgt    4140
ctaaaaaaat gctttgccgt atattatccc acttaatctc caccactatg ctgtacatag    4200
gagccacaac tcctagacaa caaataaaaa tcctatcact tttcaaatcc taacattttc    4260
atatgacaaa gccagaactc aaaatccaga cctctagagt cccagatcag gaaaggaaga    4320
aacgccaagt caaagagaag cttctttaga ataatctgct tttctggatt attcacacca    4380
tgggtcagct ccccacttga agtcagaacc aagctccaat ttcagtgaac caccatcatg    4440 cttttgaccag gagattctct cagaaatgtg gggtcccatt gagtaggcct gaagacagag    4500
attgacaggc ctatgtgagc ctggaggagt tcttttagg ggctggataa tgtcaagaac    4560
agagaacaac tccagagaag gcacacacgc cttcaaaccc atcccctcat ggggagaaag    4620
cagccaggaa ctcaggcctc aagtgttcta ggtgtggtct cccaaggaaa cgggctcact    4680
tagtttgggg aaaccttcaa accctgcact gagtcctatg tagactggga cagaaggtgg    4740
acaatgtaat cccctgagcc ctcaacctcc tcctggagag atgacaagat taagatttct    4800
ctaccagaac cctcaacaga cacatcccag aatctcccca agtgaaatgt gctctaccta    4860
ccgtccctga gagcccaggg gtgtgaaccc agagggcagg tgtggtgggg aagggaggag    4920
ggagaaagaa aagggatggc tgggagttag agaaaggctc ctatccagga cctgcctgca    4980
aggatcccag gtatcagcca gcccaaccta gcccttgttg acttagcagg tgacagtttg    5040
gggaagaagg ggaggaggat gcggaagtca cacctctcca ggcttggttc ccattggccc    5100
ttgatatcct taaaagggcc cagcaatttc agcatcctta ttccccagac cttctgcaga    5160
```

```
ttctgtggtt atactcactc ctcatcccaa aga                            5193

<210> SEQ ID NO 6
<211> LENGTH: 2436
<212> TYPE: DNA
<213> ORGANISM: Homo sapiens

<400> SEQUENCE: 6
tctcgagacc cagcccagtt aagcagagga aattacagca gggcaccaat gccaagacgt    60
aggcatcacc aggagctatc tctgaagtcg tcctaccaca catgccaaag caagagaggg   120
agcaggagga acaaatgcct tgatctctcc cttttcccac cctcccatct cccacctgtg   180
tctcccattg gccaaactca actcgaagct agagggcatg ggagcccagg tgatacagcc   240
catagaggca tccttccaga ccagtgcaga gatgagagag aataaacctg aggcagaggg   300
gagagaggta caacgagcag cccatgagac aagacacaga tcagcgaact gacagtcatc   360
atggaggtca gataacctag aaaacaagac atcacacaga gcagcccctc acccatatcc   420
atgaggtccg tcaagacatt gcacagagca gcctctcacc catatccatg aggtctgcct   480
ctttaatcta tgcacccaat tctttcccag gctctataat ttggggtaac atttctctgg   540
gccctgttat agaataatga aaattttcta taaaacaaat gtccttactt tcacctcatc   600
cctatttatg taaatgcttg cctctttaat tactgaggcc aggaggaaga tttgggagag   660
gaaagggcta tgcggtgaca tttgaaaaga ccctgctctg tgacagttct agtgttgacg   720
ccaaagttct catttcctct tagaaaagtc ttgtgcaaat agcataattt gctcctgttg   780
acttttttaa tgtgctcatg gagactgctc gggatctaga tctgtttggg atctgcagga   840
cttctccttc tgcagtgtac acacacgtgc acacacgtat gtgcacatac ccagggcact   900
ggtgccatca aactttctc ttgttcttca gccttcccca ttccaggtaa ggccaccacc   960
accttcaagg ctcccaggcc cagaccctca ggcaggtagc aattgccaag ctttaatgt   1020 cccaccccat taattttatc ttcctttatc tcctgaaaag attaatgttc taaaccctgg   1080
cacccaaaac accctcatgt tgaaaactct tcaatacccc cttctcacac tcatcttcag   1140
agctaccatg aggcagagaa gcctccggaa tcagcccaca tggggctggg tgaatgccaa   1200
caccaagcaa ggggaaagtc acaaattgac atccagcacc ttattctcca cccttcagcc   1260
cctcaactga ctcctgctcc acggcccgtt ctattaatat ctagcattta gcaccagcct   1320
ggacaaaaac ctacttggaa agatggtaca agaaccccac acaactccat gaacttcgc    1380 tgtctaaaaa aatgctttgc cgtatattat cccacttaat ctccaccact atgctgtaca   1440
taggagccac aactcctaga caacaaataa aaatcctatc acttttcaaa tcctaacatt   1500
ttcatatgac aaagccagaa ctcaaaatcc agacctctag agtcccagat caggaaagga   1560
agaaacgcca gtcaaagag aagcttcttt agaataatct gcttttctgg attattcaca    1620
ccatgggtca gctccccact tgaagtcaga accaagctcc aatttcagtg aaccaccatc   1680
atgctttgac caggagattc tctcagaaat gtgggtccc attgagtagg cctgaagaca    1740
gagattgaca ggcctatgtg agcctggagg agttcttttt aggggctgga taatgtcaag   1800
aacagagaac aactccagag aaggcacaca cgccttcaaa cccatcccct catggggaga   1860
aagcagccag gaactcaggc ctcaagtgtt ctaggtgtgg tctcccaagg aaacgggctc   1920
acttagtttg gggaaacctt caaaccctgc actgagtcct atgtagactg ggacagaagg   1980
tggacaatgt aatcccctga gccctcaacc tcctcctgga gagatgacaa gattaagatt   2040
```

-continued

| | |
|---|---|
| tctctaccag aaccctcaac agacacatcc cagaatctcc ccaagtgaaa tgtgctctac | 2100 |
| ctaccgtccc tgagagccca ggggtgtgaa cccagagggc aggtgtggtg gggaagggag | 2160 |
| gagggagaaa gaaagggat ggctgggagt tagagaaagg ctcctatcca ggacctgcct | 2220 |
| gcaaggatcc caggtatcag ccagcccaac ctagcccttg ttgacttagc aggtgacagt | 2280 |
| ttggggaaga aggggaggag gatgcggaag tcacacctct ccaggcttgg ttcccattgg | 2340 |
| cccttgatat ccttaaaagg gcccagcaat ttcagcatcc ttattcccca gaccttctgc | 2400 |
| agattctgtg gttatactca ctcctcatcc aaaga | 2436 |

<210> SEQ ID NO 7
<211> LENGTH: 1620
<212> TYPE: DNA
<213> ORGANISM: Homo sapiens

<400> SEQUENCE: 7

| | |
|---|---|
| tagatctgtt tgggatctgc aggacttctc cttctgcagt gtacacacac gtgcacacac | 60 |
| gtatgtgcac atacccaggg cactggtgcc atcaaaactt tctcttgttc ttcagccttc | 120 |
| cccattccag gtaaggccac caccaccttc aaggctccca ggcccagacc ctcaggcagg | 180 |
| tagcaattgc caaggcttta atgtcccacc ccattaattt tatcttcctt tatctcctga | 240 |
| aaagattaat gttctaaacc ctggcaccca aaacaccctc atgttgaaaa ctcttcaata | 300 |
| cccccttctc acactcatct tcagagctac catgaggcag agaagcctcc ggaatcagcc | 360 |
| cacatggggc tgggtgaatg ccaacaccaa gcaaggggaa agtcacaaat tgacatccag | 420 |
| caccttattc tccacccttc agcccctcaa ctgactcctg ctccacggcc cgttctatta | 480 |
| atatctagca tttagcacca gcctggacaa aaacctactt ggaaagatgg tacaagaacc | 540 |
| ccacacaact ccatagaact tcgctgtcta aaaaaatgct ttgccgtata ttatcccact | 600 |
| taatctccac cactatgctg tacataggag ccacaactcc tagacaacaa ataaaaatcc | 660 |
| tatcactttt caaatcctaa cattttcata tgacaaagcc agaactcaaa atccagacct | 720 |
| ctagagtccc agatcaggaa aggaagaaac gccaagtcaa agagaagctt ctttagaata | 780 |
| atctgctttt ctggattatt cacaccatgg gtcagctccc cacttgaagt cagaaccaag | 840 |
| ctccaatttc agtgaaccac catcatgctt tgaccaggag attctctcag aaatgtgggg | 900 |
| tcccattgag taggcctgaa gacagagatt gacaggccta tgtgagcctg gaggagttct | 960 |
| ttttaggggc tggataatgt caagaacaga gaacaactcc agagaaggca cacacgcctt | 1020 |
| caaacccatc ccctcatggg gagaaagcag ccaggaactc aggcctcaag tgttctaggt | 1080 |
| gtggtctccc aaggaaacgg gctcacttag tttggggaaa ccttcaaacc ctgcactgag | 1140 |
| tcctatgtag actgggacag aaggtggaca atgtaatccc ctgagccctc aacctcctcc | 1200 |
| tggagagatg acaagattaa gatttctcta ccagaaccct caacagacac atcccagaat | 1260 |
| ctccccaagt gaaatgtgct ctacctaccg tccctgagag cccaggggtg tgaacccaga | 1320 |
| gggcaggtgt ggtggggaag ggaggaggga gaaagaaaag ggatggctgg gagttagaga | 1380 |
| aaggctccta tccaggacct gcctgcaagg atcccaggta tcagccagcc caacctagcc | 1440 |
| cttgttgact tagcaggtga cagtttgggg aagaagggga ggaggatgcg gaagtcacac | 1500 |
| ctctccaggc ttggttccca ttggcccttg atatccttaa aagggcccag caatttcagc | 1560 |
| atccttattc cccagacctt ctgcagattc tgtggttata ctcactcctc atcccaaaga | 1620 |

<210> SEQ ID NO 8
<211> LENGTH: 862

-continued

```
<212> TYPE: DNA
<213> ORGANISM: Homo sapiens

<400> SEQUENCE: 8
aaagagaagc ttctttagaa taatctgctt ttctggatta ttcacaccat gggtcagctc      60
cccacttgaa gtcagaacca agctccaatt tcagtgaacc accatcatgc tttgaccagg     120
agattctctc agaaatgtgg ggtcccattg agtaggcctg aagacagaga ttgacaggcc     180
tatgtgagcc tggaggagtt cttttaggg gctggataat gtcaagaaca gagaacaact      240
ccagagaagg cacacacgcc ttcaaaccca tcccctcatg gggagaaagc agccaggaac     300
tcaggcctca agtgttctag gtgtggtctc ccaaggaaac gggctcactt agtttgggga     360
aaccttcaaa ccctgcactg agtcctatgt agactgggac agaaggtgga caatgtaatc     420
ccctgagccc tcaacctcct cctggagaga tgacaagatt aagatttctc taccagaacc     480
ctcaacagac acatcccaga atctccccaa gtgaaatgtg ctctacctac cgtccctgag     540
agcccagggg tgtgaaccca gagggcaggt gtggtgggga agggaggagg gagaaagaaa     600
agggatggct gggagttaga gaaaggctcc tatccaggac ctgcctgcaa ggatcccagg     660
tatcagccag cccaacctag cccttgttga cttagcaggt gacagtttgg ggaagaaggg     720
gaggaggatg cggaagtcac acctctccag gcttggttcc cattggccct tgatatcctt     780
aaaagggccc agcaatttca gcatccttat tccccagacc ttctgcagat tctgtggtta     840
tactcactcc tcatcccaaa ga                                              862

<210> SEQ ID NO 9
<211> LENGTH: 19
<212> TYPE: PRT
<213> ORGANISM: Homo sapiens

<400> SEQUENCE: 9

Met Lys Phe Thr Thr Leu Leu Phe Leu Ala Ala Val Ala Gly Ala Leu
1               5                   10                  15

Val Tyr Ala

<210> SEQ ID NO 10
<211> LENGTH: 119
<212> TYPE: PRT
<213> ORGANISM: Homo sapiens

<400> SEQUENCE: 10

Glu Asp Ala Ser Ser Asp Ser Thr Gly Ala Asp Pro Ala Gln Glu Ala
1               5                   10                  15

Gly Thr Ser Lys Pro Asn Glu Glu Ile Ser Gly Pro Ala Glu Pro Ala
                20                  25                  30

Ser Pro Pro Glu Thr Thr Thr Thr Ala Gln Glu Thr Ser Ala Ala Ala
            35                  40                  45

Val Gln Gly Thr Ala Lys Val Thr Ser Ser Arg Gln Glu Leu Asn Pro
        50                  55                  60

Leu Lys Ser Ile Val Glu Lys Ser Ile Leu Thr Gln Gln Ala Leu
65                  70                  75                  80

Ala Lys Ala Gly Lys Gly Met His Gly Gly Val Pro Gly Gly Lys Gln
                85                  90                  95

Phe Ile Glu Asn Gly Ser Glu Phe Ala Gln Lys Leu Leu Lys Lys Phe
            100                 105                 110

Ser Leu Leu Lys Pro Trp Ala
        115
```

<210> SEQ ID NO 11
<211> LENGTH: 23
<212> TYPE: DNA
<213> ORGANISM: Artificial
<220> FEATURE:
<223> OTHER INFORMATION: Oligonucleotide probe for detecting genomic
      lacritin clone
<220> FEATURE:
<221> NAME/KEY: primer_bind
<222> LOCATION: (1)..(23)

<400> SEQUENCE: 11
agctggggca caggcacccg cac                                            23

<210> SEQ ID NO 12
<211> LENGTH: 23
<212> TYPE: DNA
<213> ORGANISM: Artificial
<220> FEATURE:
<223> OTHER INFORMATION: Oligonucleotide probe for detecting genomic
      lacritin clone
<220> FEATURE:
<221> NAME/KEY: primer_bind
<222> LOCATION: (1)..(23)

<400> SEQUENCE: 12
ggggttctgg ggctgcagct ggg                                            23

<210> SEQ ID NO 13
<211> LENGTH: 21
<212> TYPE: DNA
<213> ORGANISM: Artificial
<220> FEATURE:
<223> OTHER INFORMATION: PCR primer corresponding to nucleotides 523
      to 503 of the lacritin gene
<220> FEATURE:
<221> NAME/KEY: primer_bind
<222> LOCATION: (1)..(21)

<400> SEQUENCE: 13
cgctacaagg gtatttaagg c                                              21

<210> SEQ ID NO 14
<211> LENGTH: 20
<212> TYPE: DNA
<213> ORGANISM: Artificial
<220> FEATURE:
<223> OTHER INFORMATION: PCR primer for exon 1 of the lacritin gene
<220> FEATURE:
<221> NAME/KEY: primer_bind
<222> LOCATION: (1)..(20)

<400> SEQUENCE: 14
actcactcct catcccaaag                                                20

<210> SEQ ID NO 15
<211> LENGTH: 19
<212> TYPE: DNA
<213> ORGANISM: Artificial
<220> FEATURE:
<223> OTHER INFORMATION: PCR primer for exon 5 of the lacritin gene
<220> FEATURE:
<221> NAME/KEY: primer_bind
<222> LOCATION: (1)..(19)

<400> SEQUENCE: 15
ttttcagctt ctcatgccc                                                 19

OCULAR TEAR GROWTH FACTOR-LIKE PROTEIN

RELATED APPLICATION

This application is a divisional application of U.S. application Ser. No. 10/468,372 filed Aug. 19, 2003 which is a national stage application of PCT/US02/04971 filed Feb. 20, 2002 that claims priority under 35 USC, §119(e) to U.S. Provisional Application Ser. No. 60/269,900, filed Feb. 20, 2001, the disclosures of which are incorporated herein in their entirety.

US GOVERNMENT RIGHTS

This invention was made with United States Government support under Grant No. R01 EY09747 and R01 EY13143, awarded by National Institutes of Health. The United States Government has certain rights in the invention.

FIELD OF THE INVENTION

The present invention is directed to a novel ocular protein, designated lacritin, and nucleic acid sequences encoding that protein. In one embodiment of the invention compositions comprising lacritin are used to enhance corneal wound healing, and/or treat patients having deficient tear output.

BACKGROUND OF THE INVENTION

Health of the ocular surface is dependent on tear fluid secretions from the lacrimal gland. The lacrimal acinar cells comprising the lacrimal gland are polarized and highly differentiated tear secreting cells that adhere to a complex periacinar basement membrane. The bulk of the apical cell cytoplasm contains large secretory granules packed with tear proteins. Known tear proteins include: lysozyme, which plays a prominent bacteriocidal role on the corneal surface; lactoferrin, which functions as both a bacteriocidal agent and as a potential inhibitor of complement activation; secretory component, which regulates the transcellular movement of IgA into acini lumen where it acts on the corneal surface to inhibit bacterial adhesion; and tear lipocalins (tear-specific prealbumin) and growth factors TGFα, TGFβ and EGF the functions of which are not known. In rats, peroxidase is a tear component which has served as a convenient marker in experimental studies. Tears not only have an important bacteriocidal role, they also keep the cornea clean and lubricated and are important for the well-being of the corneal epithelium.

When lacrimal acinar cell tear output is collectively deficient, 'Dry Eye' (also known as keratoconjunctivitis sicca [KCS]); is the result. Dry Eye is a common ocular manifestation of Sjogren's syndrome, an autoimmune disease with unknown etiology that affects millions of people worldwide. Most commonly affected are post-menopausal women with varying degrees of severity. If untreated, Dry Eye can lead to corneal abrasion, ulceration, bacterial infection and loss of vision. Molecular mechanisms underlying the pathogenic decline of secretory output by the main lacrimal gland are potentially multiple. Lacrimal glands of Sjogren's syndrome patients contain foci of B and T lymphocytes whose pathogenic expansion, possibly due to viral insult, can destroy lacrimal acini. However, acinar volume loss often appears insufficient relative to the theoretical overcapacity of the main lacrimal gland. Estimates suggest a potential secretory output up to ten-fold greater than is required to maintain a normal aqueous tear film layer. Other mechanisms therefore warrant attention, such as aberrant secretion of one or several common cytokines that may directly or indirectly alter lacrimal acinar cell function and/or lead to a decline in neural innervation. Novel autocrine/paracrine factor(s) released by lacrimal acinar cells into the tear film may be required for the health of the lacrimal secretory machinery, ductal system and corneal epithelium. The periacinar basement membrane is also required for normal secretory function, in part via 'BM180' whose apparent synergy with laminin-1 promotes stimulated tear secretion. Alteration of each of these factors, together or independent of hormonal changes, could contribute to decreased secretory capacity.

Existing protocols for treating Dry Eye suffer from several limitations. In particular, topical artificial tear replacement fluids are widely distributed by a number of pharmaceutical companies, but the efficacy is poor and short-lived. This lack of efficacy is due in part to the fact that constituents of natural human tears are only partially known.

The present invention is directed to a novel human extracellular glycoprotein termed 'lacritin' that is remarkably reduced in Sjogren's syndrome. Furthermore lacritin has been found to act in an autocrine manner to enhance unstimulated (but not stimulated) tear secretion. Lacritin is produced by lacrimal acinar cells and released for the most part into tear fluid—much like acinar cell-expressed TGFβ's. This glycoprotein acts like a growth factor when added in purified recombinant form to cultures of human corneal epithelial cells, and in a feedback mechanism, it also appears to act on the same lacrimal gland cells that produce it. Accordingly in one embodiment of the present invention, lacritin is included as an active agent in artificial tear products.

SUMMARY OF THE INVENTION

The present invention is directed to the isolation and characterization of a novel lacrimal gland protein and the nucleic acid sequences encoding that protein. Purified recombinant lacritin has activity as a growth factor on both human corneal epithelial cells and on the lacrimal acinar cells that produce it. Accordingly, in one embodiment of the present invention a method is provided for treating Dry Eye and other disorders requiring the wetting of the eye by administering compositions comprising a lacritin polypeptide. In addition, since the gene promoter regulating lacritin gene expression is the most specific of any previously described-lacrimal gland gene, the regulatory elements of this gene could be used to express other gene products in the eye.

BRIEF DESCRIPTION OF THE DRAWINGS

FIG. 2A is a graphic representation of the number of human salivary gland (HSG) cells was determined four days after administering various amounts of lacritin (0 to 10 ng/ml of lacritin) to HSG cells in serum-free medium. FIG. 2B is a bar graph representing the proliferation of HSG cells upon administration of BSA (lane 1; 10 ng/ml) or serum (lane 2; 10%) was added for the same period of time. All experiments were performed on laminin-1-(0.05 μM) coated wells.

DETAILED DESCRIPTION OF THE INVENTION

Definitions

Figure 1:
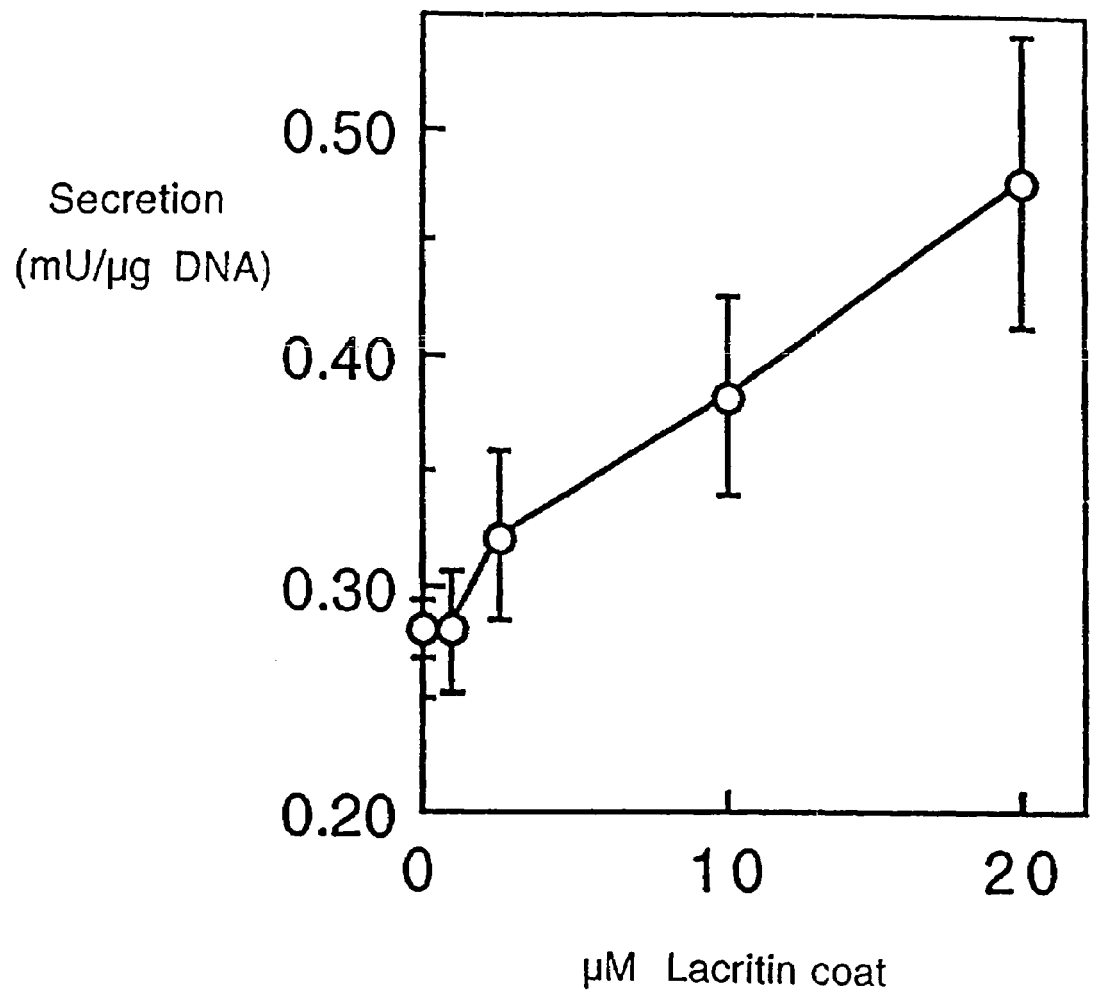
FIG. 1 is a graphic representation that shows recombinant lacritin enhances unstimulated secretion by isolated rat lacrimal acinar cells. Enhancement of unstimulated secretion was observed in the presence of increasing amounts of lacritin on lacritin-coated wells.

In describing and claiming the invention, the following terminology will be used in accordance with the definitions set forth below.

As used herein, "nucleic acid," "DNA," and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention.

The term "peptide" encompasses a sequence of 3 or more amino acids wherein the amino acids are naturally occurring or synthetic (non-naturally occurring) amino acids. Peptide mimetics include peptides having one or more of the following modifications:

1. peptides wherein one or more of the peptidyl —C(O)NR— linkages (bonds) have been replaced by a non-peptidyl linkage such as a —CH2-carbamate linkage (—CH2OC(O)NR—), a phosphonate linkage, a —CH2-sulfonamide (—CH 2-S(O)2NR—) linkage, a urea (—NHC(O)NH—) linkage, a —CH2-secondary amine linkage, or with an alkylated peptidyl linkage (—C(O)NR—) wherein R is C1-C4 alkyl;
2. peptides wherein the N-terminus is derivatized to a —NRR1 group, to a —NRC(O)R group, to a —NRC(O)OR group, to a —NRS(O)2R group, to a —NHC(O)NHR group where R and R1 are hydrogen or C1-C4 alkyl with the proviso that R and R1 are not both hydrogen;
3. peptides wherein the C terminus is derivatized to —C(O)R2 where R2 is selected from the group consisting of C1-C4 alkoxy, and —NR3R4 where R3 and R4 are independently selected from the group consisting of hydrogen and C1-C4 alkyl.

Naturally occurring amino acid residues in peptides are abbreviated as recommended by the IUPAC-IUB Biochemical Nomenclature Commission as follows: Phenylalanine is Phe or F; Leucine is Leu or L; Isoleucine is Ile or I; Methionine is Met or M; Norleucine is Nle; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; Glycine is Gly or G, and X is any amino acid. Other naturally occurring amino acids include, by way of example, 4-hydroxyproline, 5-hydroxylysine, and the like.

Synthetic or non-naturally occurring amino acids refer to amino acids which do not naturally occur in vivo but which, nevertheless, can be incorporated into the peptide structures described herein. The resulting "synthetic peptide" contain amino acids other than the 20 naturally occurring, genetically encoded amino acids at one, two, or more positions of the peptides. For instance, naphthylalanine can be substituted for trytophan to facilitate synthesis. Other synthetic amino acids that can be substituted into peptides include L-hydroxypropyl, L-3,4-dihydroxyphenylalanyl, alpha-amino acids such as L-alpha-hydroxylysyl and D-alpha-methylalanyl, L-alpha.-methylalanyl, beta.-amino acids, and isoquinolyl. D amino acids and non-naturally occurring synthetic amino acids can also be incorporated into the peptides. Other derivatives include replacement of the naturally occurring side chains of the 20 genetically encoded-amino acids (or any L or D amino acid) with other side chains.

As used herein, the term "conservative amino acid substitution" are defined herein as exchanges within one of the following five groups:

I. Small aliphatic, nonpolar or slightly polar residues:
   Ala, Ser, Thr, Pro, Gly;
II. Polar, negatively charged residues and their amides:
   Asp, Asn, Glu, Gln;
III. Polar, positively charged residues:
   His, Arg, Lys;
IV. Large, aliphatic, nonpolar residues:
   Met Leu, Ile, Val, Cys
V. Large, aromatic residues:
   Phe, Tyr, Trp A "polylinker" is a nucleic acid sequence that comprises a series of three or more different restriction endonuclease recognitions sequences closely spaced to one another (i.e. less than 10 nucleotides between each site).

As used herein, the term "vector" is used in reference to nucleic acid molecules that has the capability of replicating autonomously in a host cell, and optionally may be capable of transferring DNA segment(s) from one cell to another. Vectors can be used to introduce foreign DNA into host cells where it can be replicated (i.e., reproduced) in large quantities. Examples of vectors include plasmids, cosmids, lambda phage vectors, viral vectors (such as retroviral vectors).

As used herein a "gene" refers to the nucleic acid coding sequence as well as the regulatory elements necessary for the DNA sequence to be transcribed into messenger RNA (MRNA) and then translated into a sequence of amino acids characteristic of a specific polypeptide.

A "marker" is an atom or molecule that permits the specific detection of a molecule comprising that marker in the presence of similar molecules without such a marker. Markers include, for example radioactive isotopes, antigenic determinants, nucleic acids available for hybridization, chromophors, fluorophors, chemiluminescent molecules, electrochemically detectable molecules, molecules that provide for altered fluorescence-polarization or altered light-scattering and molecules that allow for enhanced survival of an cell or organism (i.e. a selectable marker). A reporter gene is a gene that encodes for a marker.

A promoter is a DNA sequence that directs the transcription of a DNA sequence, such as the nucleic acid coding sequence of a gene. Typically, a promoter is located in the 5' region of a gene, proximal to the transcriptional start site of a structural gene. Promoters can be inducible (the rate of transcription changes in response to a specific agent), tissue specific (expressed only in some tissues), temporal specific (expressed only at certain times) or constitutive (expressed in all tissues and at a constant rate of transcription).

A core promoter contains essential nucleotide sequences for promoter function, including the TATA box and start of transcription. By this definition, a core promoter may or may not have detectable activity in the absence of specific sequences that enhance the activity or confer tissue specific activity.

An "enhancer" is a DNA regulatory element that can increase the efficiency of transcription, regardless of the distance or orientation of the enhancer relative to the start site of transcription.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A."

As used herein, the term "hybridization" is used in reference to the pairing of complementary nucleic acids. Hybridization and the strength of hybridization (i.e., the strength of the association between the nucleic acids) is impacted by such factors as the degree of complementarity between the nucleic acids, stringency of the conditions involved, the length of the formed hybrid, and the G:C ratio within the nucleic acids.

As used herein, the term "purified" and like terms relate to the isolation of a molecule or compound in a form that is substantially free of contaminants normally associated with the molecule or compound in a native or natural environment.

As used herein, the term "lacritin polypeptide" and like terms refers to peptides comprising the amino acid sequence of SEQ ID NO: 4 and biologically active fragments thereof.

As used herein, the term "biologically active fragments" or "bioactive fragment" of an lacritin polypeptide encompasses natural or synthetic portions of the amino acid sequence MKFTTLLFLMVAGALVYAEDASSDSTGADPAQEAGTSKPNEEI SGPAEPASPPETTTAQETSMAVQG-TAKVTSSRQELNPLKSIVEKSILLTEQALAKAGKGM HGGVPGGKQFIENGSE-FAQKLLKKFSLLKPWA (SEQ ID NO: 4) that are capable of specific binding to at least one of the natural ligands of the native lacritin polypeptide.

"Operably linked" refers to a juxtaposition wherein the components are configured so as to perform their usual function. Thus, control sequences or promoters operably linked to a coding sequence are capable of effecting the expression of the coding sequence.

As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents.

As used herein, the term "treating" includes alleviating the symptoms associated with a specific disorder or condition and/or preventing or eliminating said symptoms.

The Invention

The present invention is directed to a novel human growth factor-like molecule, 'lacritin' and compositions comprising lacritin. The invention also encompasses the nucleic acid sequences encoding lacritin as well as the nucleic acid regulatory elements controlling the expression of lacritin. The full length 'lacritin' cDNA has been cloned from a human lacrimal gland library (SEQ ID NO:2), and the corresponding genomic gene (SEQ ID NO: 1) has been cloned and sequenced, including 5.2 kb of upstream and 2.8 kb of downstream genomic sequence.

In one embodiment, the present invention is directed to a purified polypeptide comprising the amino acid sequence of SEQ ID NO: 4, SEQ ID NO: 10, a bioactive fragment of SEQ ID NO: 4, or an amino acid sequence that differs from SEQ ID NO: 4 by one or more conservative amino acid substitutions. More preferably, the purified polypeptide comprises an amino acid sequence that differs from SEQ ID NO: 4 by 20 or less conservative amino acid substitutions, and more preferably by 10 or less conservative amino acid substitutions. Alternatively, the polypeptide may comprise an amino acid sequence that differs from SEQ ID NO: 4 by 1 to 5 alterations, wherein the alterations are independently selected from a single amino acid deletion, insertion or substitution. In one preferred embodiment a composition is provided comprising a polypeptide, selected from the group consisting of SEQ ID NO: 4, or SEQ ID NO: 10, and a pharmaceutically acceptable carrier.

Also encompassed in the present invention are ligands that bind to the lacritin polypeptide, including the natural receptor for lacritin, as well as methods for isolating such ligands. In one embodiment the lacritin polypeptide, or bioactive fragments thereof, is used to isolate ligands that bind to the lacritin polypeptide under physiological conditions. The method comprises the steps of contacting the lacritin polypeptide with a mixture of compounds under physiological conditions, removing unbound and non-specifically bound material, and isolating the compounds that remain bound to the lacritin polypeptides. Typically, the lacritin polypeptide will be bound to a solid support using standard techniques to allow for rapid screening of compounds. The solid support can be selected from any surface that has been used to immobilize biological compounds and includes but is not limited to polystyrene, agarose, silica or nitrocellulose. In one embodiment the solid surface comprises functionalized silica or agarose beads. Screening for such compounds can be accomplished using libraries of pharmaceutical agents and standard techniques known to the skilled practitioner.

In an alternative embodiment a cell based assay is used to detect ligands that bind to lacritin (including lacritin's natural receptor). The method comprises contacting transfected cells with lacritin and isolating the relevant genes from those cells that display lacritin-dependent calcium signaling. More particularly, in one embodiment, previously described pools of orphan G protein coupled receptor cDNA's will be expressed in cell lines such as HEK293T and RH7777 cells, and the transfected cells will be contacted with lacritin. A transfectant that displays lacritin-dependent calcium signaling should be expressing the receptor. If the receptor is not detected in the available pool of orphan G protein coupled receptor cDNA's, cDNA's from a salivary ductal cell library will be transfected into 293T cells, and expressors screened by FACS with fluorescently labeled lacritin. In accordance with one embodiment cells expressing receptors that can be activated by lacritin will be detected using a cell free system. More particularly, receptor activity will be detected via a $GTP[_{\gamma35} S]$ binding assay using isolated cell membranes from the transfected cells.

In one aspect of the invention a method for detecting the lacritin receptor is provided. The method comprises the steps of providing a cell that has been transfected with nucleic acid sequences that encode for potential cell receptors, contacting the transfected cells with lacritin and detecting those cells that display lacritin-dependent calcium signaling. If the cells displaying lacritin-dependent calcium signaling were transfected with more than one protein encoding gene sequence, than the nucleic acid sequences encoding for the lacritin receptor will be identified by sequence analysis or other molecular technique. For example, the introduced recombinant nucleic acids will be isolated from the signaling cells and further subcloned with the resulting subclones used to transfect cells to determine the unique sequence responsible for conferring lacritin-dependent calcium signaling to a cell.

The present invention also encompasses nucleic acid sequences that encode the lacritin polypeptide and derivatives thereof. In particular the present invention is directed to nucleic acid sequences comprising the sequence of SEQ ID NO: 1, SEQ ID NO: 2, SEQ ID NO: 3, or fragments thereof. In one embodiment, purified nucleic acids comprising at least 8 contiguous nucleotides (i.e., a hybridizable portion) that are identical to any 8 contiguous nucleotides of SEQ ID NO: 1 are provided. In other embodiments, the nucleic acids comprises at least 25 (contiguous) nucleotides, 50 nucleotides, 100 nucleotides, 200 nucleotides, or 500 nucleotides of SEQ ID NO: 1. In another embodiment the nucleic acid sequence comprises the sequence of SEQ ID NO: 3 or a 25 bp nucleic acid sequence that is identical to a contiguous 25 bp sequence of SEQ ID NO: 3.

The present invention also includes nucleic acids that hybridize (under conditions defined herein) to all or a portion of the nucleotide sequence represented by SEQ ID NO:1 or its complement. The hybridizing portion of the hybridizing nucleic acids is typically at least 15 (e.g., 20, 25, 30, or 50) nucleotides in length. Hybridizing nucleic acids of the type described herein can be used, for example, as a cloning probe, a primer (e.g., a PCR primer), or a diagnostic probe. It is anticipated that the DNA sequence of SEQ ID NO: 1, or fragments thereof can be used as probes to detect homologous genes from other vertebrate species.

Nucleic acid duplex or hybrid stability is expressed as the melting temperature or Tm, which is the temperature at which a nucleic acid duplex dissociates into its component single stranded DNAs. This melting temperature is used to define the required stringency conditions. Typically a 1% mismatch results in a 1° C. decrease in the Tm, and the temperature of the final wash in the hybridization reaction is reduced accordingly (for example, if two sequences having >95% identity, the final wash temperature is decreased from the Tm by 5° C.). In practice, the change in Tm can be between 0.5° C. and 1.5° C. per 1% mismatch.

The present invention is directed to the nucleic acid sequence of SEQ ID NO: 1 and nucleic acid sequences that hybridize to that sequence (or fragments thereof) under stringent or highly stringent conditions. In one embodiment the invention is directed to a purified nucleic acid sequence that hybridizes to a 100 nucleotide fragment of SEQ ID NO: 1 or its complement under stringent conditions. In accordance with the present invention highly stringent conditions are defined as conducting the hybridization and wash conditions at no lower than −5° C. Tm. Stringent conditions are defined as involve hybridizing at 68° C. in 5×SSC/5× Denhardt's solution/1.0% SDS, and washing in 0.2×SSC/ 0.1% SDS at 68° C. Moderately stringent conditions include hybridizing at 68° C. in 5×SSC/5× Denhardt's solution/ 1.0% SDS and washing in 3×SSC/0.1% SDS at 42° C. Additional guidance regarding such conditions is readily available in the art, for example, by Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.) at Unit 2.10.

In another embodiment of the present invention, nucleic acid sequences encoding the lacritin polypeptide can be inserted into expression vectors and used to transfect cells to express recombinant lacritin in the target cells. In accordance with one embodiment, the nucleic acid sequence of SEQ ID NO: 3 are inserted into a eukaryotic expression vector in a manner that operably links the gene sequences to the appropriate regulatory sequences, and lacritin is expressed in a eukaryotic host cell. Suitable eukaryotic host cells and vectors are known to those skilled in the art. In particular, nucleic acid sequences encoding lacritin may be added to a cell or cells in vitro or in vivo using delivery mechanisms such as liposomes, viral based vectors, or microinjection. Accordingly, one aspect of the present invention is directed to transgenic cell lines that contain recombinant genes that express the lacritin polypeptide of SEQ ID NO: 4.

The present invention is also directed to nucleic acid constructs for expressing heterologous genes under the control of the lacritin gene promoter. In accordance with one embodiment a nucleic acid construct is provided comprising a nucleic acid sequence selected from the group consisting of SEQ ID NO: 5, SEQ ID NO: 6, SEQ ID NO: 7 and SEQ ID NO: 8 operably linked to a heterologous gene. In accordance with one embodiment the heterologous gene is a reporter gene that encodes for a marker. The marker can be any gene product that produces a detectable signal and includes proteins capable of emitting light such as Green Fluorescent Protein (GFP) (Chalfie et al., 1994, Science 11: 263:802-805) or luciferase (Gould et al., 1988, Anal. Biochem. 15: 175: 5-13), as well as proteins that can catalyze a substrate (e.g., such as β-galactosidase). The marker may also comprise intracellular or cell surface proteins that are detectable by antibodies. Reporter molecules additionally, or alternatively, can be detected by virtue of a unique nucleic acid sequence not normally contained within the cell.

As used herein, "GFP" refers to a member of a family of naturally occurring fluorescent proteins, whose fluorescence is primarily in the green region of the spectrum. The term includes mutant forms of the protein with altered or enhanced spectral properties. Some of these mutant forms are described in Cormack, et al., 1996, Gene 173: 33-38 and Ormo, 1996, Science 273:1392-1395, the entireties of which are incorporated herein by reference. The term also includes polypeptide analogs, fragments or derivatives of GFP polypeptides which differ from naturally-occurring forms by the identity or location of one or more amino acid residues, (e.g., by deletion, substitution or insertion) and which share some or all of the properties of the naturally occurring forms so long as they generate detectable signals (e.g., fluorescence). Wild type GFP absorbs maximally at 395 nm and emits at 509 nm. High levels of GFP expression have been obtained in cells ranging from yeast to human cells. The term also includes Blue Fluorescent Protein (BFP), the coding sequence for which is described in Anderson, et al., 1996, Proc. Natl. Acad. Sci. USA 93:16, 8508-8511, incorporated herein by reference.

Another embodiment of the present invention comprises antibodies that are generated against the lacritin polypeptide. These antibodies can be formulated with standard carriers and optionally labeled to prepare therapeutic or diagnostic compositions. Antibodies to lacritin are generated using methods that are well known in the art. Such antibodies may include, but are not limited to, polyclonal, monoclonal, chimeric (i.e "humanized" antibodies), single chain (recombinant), Fab fragments, and fragments produced by a Fab expression library. These antibodies can be used as diagnostic agents for the diagnosis of conditions or diseases characterized by expression or overexpression of lacritin, or in assays to monitor patients being treated for a conditions or diseases characterized by inappropriate lacritin expression. The antibodies useful for diagnostic purposes may be prepared in the same manner as those described above for therapeutics. The antibodies may be used with or without modification, and may be labeled by joining them, either covalently or non-covalently, with a marker. In accordance with one embodiment an antibody is provided that specifically binds to the protein of SEQ ID NO: 4, and more preferably the antibody is a monoclonal antibody.

The invention also encompasses antibodies, including anti-idiotypic antibodies, antagonists and agonists, as well as compounds or nucleotide constructs that inhibit expression of the lacritin gene (transcription factor inhibitors, antisense and ribozyme molecules, or gene or regulatory sequence replacement constructs), or promote expression of lacritin (e.g., expression constructs wherein the lacritin coding sequences, such as SEQ ID NO: 3 are operatively associated with expression control elements such as promoters, promoter/enhancers, etc.).

The present invention also encompasses antigenic compositions for raising antibodies against lacritin. In one embodiment an antigenic composition is provided comprising the polypeptide of SEQ ID NO: 4 or an antigenic fragment thereof.

Lacritin has mitogenic activity, enhances unstimulated but not stimulated secretion, and promotes signaling in both lacrimal acinar and corneal epithelial cells. Recombinant lacritin prepared in *E. coli* specifically and rapidly activates both human corneal epithelial cells and mouse & rat lacrimal acinar cells—the latter in an autocrine manner to enhance tear synthesis. Lacritin is active at ng/ml levels, and contaminating bacterial LPS (endotoxin) is not detectable. The activities of purified recombinant lacritin indicate that it acts as a growth factor on both human corneal epithelial cells and on the lacrimal acinar cells that produce it. Importantly, lacritin likely acts as a growth factor only in the eye, and to a lesser extent in the salivary gland. These organ-specific beneficial effects can be used to dramatically increase the efficacy of currently available topically artificial tear products.

Current tear supplements are not popular with patients, in part because the relief obtained from such products is very brief (less than 15 min). Examples of the tear substitution approach include the use of buffered, isotonic saline solutions, aqueous solutions containing water soluble polymers that render the solutions more viscous and thus less easily shed by the eye. Tear reconstitution is also attempted by providing one or more components of the tear film such as phospholipids and oils. Examples of these treatment approaches are disclosed in U.S. Pat. No. 4,131,651 (Shah et al.), U.S. Pat. No. 4,370,325 (Packman), U.S. Pat. No. 4,409,205 (Shively), U.S. Pat. Nos. 4,744,980 and 4,883,658 (Holly), U.S. Pat. No. 4,914,088 (Glonek), U.S. Pat. No. 5,075,104 (Gressel et al.) and U.S. Pat. No. 5,294,607 (Glonek et al.) the disclosures of which are incorporated herein. Existing ophthalmic formulations may also include TGF-beta, corticosteroids or androgens. All are non-specific for the eye and have systemic effects. In contrast, lacritin is highly restricted to the eye and is a natural constituent of human tears and the tear film.

An ophthalmic formulation comprising lacritin (for example, an artificial tear fluids containing lacritin) is highly desirable due to the activity of lacritin and its localized effects. In accordance with one embodiment of the invention, compositions comprising lacritin are used to enhance corneal wound healing, and/or treat patients having deficient tear output. More particularly, lacritin is used in accordance with one embodiment to treat Dry Eye syndromes, including Sjogren's syndrome and to enhance corneal wound healing by topical application of compositions comprising the lacritin polypeptide. In accordance with one embodiment the composition comprises a pharmaceutically acceptable carrier and a pharmaceutically effective amount of substantially pure polypeptide comprising the amino acid sequence of SEQ ID NO: 4 is used to treat Dry Eye syndromes.

The lacritin compositions of the present invention can be formulated using standard ophthalmic components, and preferably the compositions are formulated as solutions, suspensions and other dosage forms for topical administration. Aqueous solutions are generally preferred, based on ease of formulation, biological compatibility (especially in view of the malady to be treated, e.g., dry eye-type diseases and disorders), as well as a patient's ability to easily administer such compositions by means of instilling one to two drops of the solutions in the affected eyes. However, the compositions may also be suspensions, viscous or semi-viscous gels, or other types of solid or semi-solid compositions.

The compositions of the present invention may include surfactants, preservative agents, antioxidants, tonicity agents, buffers, preservatives, co-solvents and viscosity building agents. Various surfactants useful in topical ophthalmic formulations may be employed in the present compositions. These surfactants may aid in preventing chemical degradation of lacritin and also prevent the lacritin from binding to the containers in which the compositions are packaged. Examples of surfactants include, but are not limited to: Cremophor.RTM. EL, polyoxyl 20 ceto stearyl ether, polyoxyl 40 hydrogenated castor oil, polyoxyl 23 lauryl ether and poloxamer 407 may be used in the compositions. Antioxidants may be added to compositions of the present invention to protect the lacritin polypeptide from oxidation during storage. Examples of such antioxidants include, but are not limited to, vitamin E and analogs thereof, ascorbic acid and derivatives, and butylated hydroxyanisole (BHA).

Existing artificial tears formulations can also be used as pharmaceutically acceptable carriers for the lacritin active agent. Thus in one embodiment, lacritin is used to improve existing artificial tear products for Dry Eye syndromes, as well as develop products to aid corneal wound healing. Examples of artificial tears compositions useful as carriers include, but are not limited to, commercial products, such as Tears Naturale.RTM., Tears Naturale II.RTM., Tears Naturale Free.RTM., and Bion Tears.RTM. (Alcon Laboratories, Inc., Fort Worth, Tex.). Examples of other phospholipid carrier formulations include those disclosed in U.S. Pat. No. 4,804,539 (Guo et al.), U.S. Pat. No. 4,883,658 (Holly), U.S. Pat. No. 4,914,088 (Glonek), U.S. Pat. No. 5,075,104 (Gressel et al.), U.S. Pat. No. 5,278,151 (Korb et al.), U.S. Pat. No. 5,294,607 (Glonek et al.), U.S. Pat. No. 5,371,108 (Korb et al.), U.S. Pat. No. 5,578,586 (Glonek et al.); the foregoing patents are incorporated herein by reference to the extent they disclose phospholipid compositions useful as phospholipid carriers of the present invention.

Other compounds may also be added to the ophthalmic compositions of the present invention to increase the viscosity of the carrier. Examples of viscosity enhancing agents include, but are not limited to: polysaccharides, such as hyaluronic acid and its salts, chondroitin sulfate and its salts, dextrans, various polymers of the cellulose family; vinyl polymers; and acrylic acid polymers. In general, the phospholipid carrier or artificial tears carrier compositions will exhibit a viscosity of 1 to 400 centipoises ("cps"). Preferred compositions containing artificial tears or phospholipid carriers and will exhibit a viscosity of about 25 cps.

Topical ophthalmic products are typically packaged in multidose form. Preservatives are thus required to prevent microbial contamination during use. Suitable preservatives include: benzalkonium chloride, chlorobutanol, benzododecinium bromide, methyl paraben, propyl paraben, phenylethyl alcohol, edetate disodium, sorbic acid, polyquaternium-1, or other agents known to those skilled in the art. Such preservatives are typically employed at a level of from 0.001 to 1.0% w/v. Unit dose compositions of the present invention will be sterile, but typically unpreserved. Such compositions, therefore, generally will not contain preservatives.

In humans, lacritin is produced by the lacrimal gland (large amounts), salivary gland (moderate), the basal cells of the corneal epithelium (based on immunostaining of human cornea by anti-lacritin antibodies; and ELISA detection of lacritin in human corneal epithelial cell cultures) and possibly in the thyroid, but not elsewhere. Lacritin enhances unstimulated but not stimulated secretion, has mitogenic activity and promotes signaling in both lacrimal acinar and corneal epithelial cells. This glycoprotein has a highly restricted glandular distribution, and this highly restricted expression pattern in combination with its functional attributes are evidence for its putative autocrine/paracrine differentiative role in the lacrimal gland and neighboring ocular system. Since the gene promoter regulating lacritin gene expression is the most specific of any previously described lacrimal gland gene, the regulatory elements of this gene could be used to express other gene products in the eye. In particular, the lacritin gene promoter can be operably linked to a wide variety of exogenous genes to regulate the expression of the gene products to the lacrimal gland and/or used as gene therapy to treat Dry Eye syndromes.

Alternatively, recombinant constructs comprising the lacritin promoter can be used to transform host cells in vitro as a means of screening for agonist and antagonist of lacritin function. In accordance with one embodiment the lacritin gene promoter is linked to a heterologous gene and reintroduced into a patient to provide gene therapeutic treatment of Dry Eye syndromes. Simply stated, the promoter could be used to artificially drive the synthesis and secretion of tear proteins in patients for which the normal gene control of these proteins may have been lost.

Physiological experiments using recombinant lacritin generated by *E. coli* suggests that it is likely a growth factor. Lacritin stimulates calcium signaling in human corneal epithelial cells and in mouse lacrimal acinar cells. It stimulates tyrosine phosphorylation in rat lacrimal acinar and human salivary ductal cells, and it enhances the quantity of tear proteins released from the. same acinar cells that produce it.

The full length 'lacritin' cDNA has been cloned from a human lacrimal gland library (SEQ ID NO:2), and the corresponding genomic gene (SEQ ID NO: 1) has been cloned and sequenced, including 5.2 kb of upstream and 2.8 kb of downstream genomic sequence. A mouse homologous gene has also been partially RT-PCR cloned, and this isolated mouse lacritin gene sequence has 99% identity to the human sequence. Expression of lacritin is remarkably restricted. Fifty-two different tissue polyA+ or total RNA's were screened and lacritin mRNA was detected only in lacrimal (very abundant), salivary (weak to moderate) and thyroid (weak) glands. A review of the literature suggests that this level of transcriptional control is unmatched by any other known lacrimal protein.

EXAMPLE 1

Isolation of the Lacritin Gene cDNA and Genomic Cloning of Lacritin

Duplicate filters containing plaques (5×10⁴ per filter) from each of ten sublibraries of a human lacrimal gland cDNA library (Dickinson & Thiesse, 1995) were prehybridized at 42° C. for 4 hr in 5× Denhardt's, 6.76×SSC, 10 mM sodium phosphate, 1 mM EDTA, 0.5% SDS and 182 µg/ml salmon sperm DNA, and then hybridized overnight at 42° C. with one of two overlapping 23-mer oligonucleotides ('S1' [AGCTGGGGCACAGGCACCCGCAC; SEQ ID NO: 11] and 'S2' [GGGGTTCTGGGGCTGCAGCTGGG; SEQ ID NO: 12]) that had been end-labeled with [32P]gATP 7000 Ci/mmole (ICN, Irvine Calif.) and purified. Final wash conditions were 2×SSC (45° C.), corresponding to 29.5° C. less than the S1 or S2 Tm (74.5° C. in 2×SSC for both). Plaques positive in both filters were picked and rescreened three times in duplicate with each oligonucleotide, giving rise to forty-seven clones. Each was subsequently reanalyzed at increasing wash stringency (−29.5, −24.5, −19.5, and −14.5° C. Tm). Inserts were excised into pBluescript and both strands sequenced via a Prizm 377 DNA Sequencer (Perkin-Elmer, Branchburg, N.J.; University of Virginia Biomolecular Research Facility). Of identical clones, most common was a novel sequence lacking homology to BM180 (BestFit quality=16, vs random quality of 17±2) from which the poly G-rich S1 and S2 oligonucleotides were derived. Predicted was a 417 bp open reading frame, whose expected protein product was designated 'lacritin', in keeping with its lacrimal gland expression. Lacritin insert was subsequently used to screen a human P1 genomic library (carried out by Genome Systems Inc; St. Louis Mo.) and three identical clones were obtained, as determined by restriction digestion and Southern analysis. The largest lacritin-positive fragment (12.4 kb) was subcloned intact into pBluescript and both strands were compieteiy sequenced. Alignment and analyses (Kumar et al, 2000) of cDNA and genomic sequence was primarily with Unix-based (Gelstart, Gap) and web-based (FASTA, BestFit, Gap) Genetics Computer Group (Madison Wis.) software using default settings and E values (FASTA) restricted to 5 or less. Genomic exon searching and identification of splice sites was facilitated by the Baylor College of Medicine Human Genome Sequencing Center web site. All nucleotide sequences have been submitted to the GenBank/EBI Data Bank with accession numbers af238867 (cDNA) and ay005150 (genomic).

Northern Analysis

Human lacrimal and submandibular glands were obtained during autopsy through the Southern division of the Cooperative Human Tissue Network within 18 hours of death and most within 8 hours to minimize autolytic degradation. The tenets of the Declaration of Helsinki were followed and informed consent and full IRB approval were obtained. Donors were without known systemic bacterial or viral infections, and tissues were normal as determined from cause of death, pathology reports and in most cases histological examination. Tissues were snap frozen in liquid nitrogen after removal and stored at −85° C. until used for RNA preparation. Total RNA was extracted from 100-300 mg of tissue using a commercial version of the acidified guanidine thiocyanate/phenol method (RNazol B, Tel-Test, The Woodlands, Tex.). Purified RNA was dissolved in diethylpyrocarbonate-treated water, and the concentration and purity determined from the A260/280 absorption values. A ratio close to 2.0 was considered acceptable. RNA integrity was initially determined by electrophoresis of ethidium bromide-complexed RNA samples in a gel containing 0.22M formaldehyde. Samples that did not show prominent 28S and 18S rRNA bands in a 1:1-2:1 ratio under UV light were rejected. For blotting, RNA (5 µg/lane) was separated on a 0.8% agarose gel under denaturing conditions (Laurie et al, 1989) and transferred to nitrocellulose. Also assayed were two purchased (cat # 7756-1 and 7751-1; Clontech Labs, Palo Alto Calif.) Northern blots with multiple human fetal and adult poly A+RNA's and a dot blot (cat # 7770-1; Clontech Labs) containing fifty different human poly A+RNA's together with control RNA's and DNA's. Blots were hybridized with [32P]-labeled lacritin insert, washed in 0.1×SSC, 0.1% SDS (Northern) or 2×SSC, 0.1% SDS (dot blot) at 55° C., and exposed to X-ray film. Dot blots were then quantitated using NIH Image by measurement of pixel gray values of individual dots.

PCR Analysis and Chromosome Mapping

Alternative splicing was examined by RT-PCR using human submandibular or lacrimal total RNA and initial priming with oligo dT, or in a gene specific manner with lacritin reverse primer CGCTACAAGGGTATTTAAGGC (SEQ ID NO: 13) corresponding to nucleotides 523 to 503 from lacritin cDNA). Subsequent amplification with lacritin forward primer ACTCACTCCTCATCCCAAAG (SEQ ID NO: 14; from exon 1; lacritin cDNA nucleotides 32 to 51) and reverse primer TTTTCAGCTTCTCATGCCC (SEQ ID NO: 15; from exon 5; lacritin cDNA nucleotides 480 to 462) involved denaturation for 2 min at 94° C., thirty cycles of amplification (94° C. for 30 sec, 52° C. for 30 sec & 72° C. for 1 min), and a final cycle for 5 min at 72° C. PCR product was analyzed in agarose gels.

For FISH mapping (Genome Systems; St. Louis, Mo.), lacritin genomic DNA was labeled with digoxigenin dUTP by nick translation and hybridized (50% formamide, 10% dextran, 2×SSC) to metaphase chromosomes from PHA-stimulated human peripheral blood lymphocytes. Following washes, specific labeling was detected with fluoresceinated antidigoxigenin antibodies and DAPI, and examined in a Nikon Labophot microscope. A total of eighty metaphase cells were analyzed with sixty exhibiting specific labeling. Confirmation was achieved by double labeling using a 12q15 marker, and by comparison with human genome project draft sequence. Photographs were taken on a Nikon AFX at a final magnification of 1,435×.

Results:

Lacrimal acinar cells are polarized exocrine secretory cells containing some mRNA's that are remarkably under-represented in gene data banks and may code for a rich array of differentiation factors—a presumption underlying the paired oligonucleotide screening of a little used human lacrimal gland cDNA library. Among the clones identified by this approach was a novel cDNA sequence (SEQ ID NO: 2) represented by several independent clones and corresponding to a 760 bp transcript and the corresponding amino acid sequence (SEQ ID NO: 4). The secreted gene product of this lacrimal gland-specific transcript was designated 'lacritin'. The lacritin nucleic acid sequence contains a 417 bp open reading frame that predicts a 14.3 kDa hydrophilic protein core with a 19 amino acid signal peptide giving rise to a mature secreted core-protein of 12.3 kDa with an isoelectric point of 5. Noteworthy is a moderately high level of glycosylation with six putative O-glycosylation sites between residues 52 and 64, and a single N-glycosylation site near the C-terminus, indicating that lacritin is a moderately well-glycosylated core protein much like the neuroglycan C glycosaminoglycan binding domain and fibulin-2 amino globular domain to which lacritin bears partial homology. Northern Blot analysis indicates a high level of lacrimal gland specificity.

In FASTA searches of the primate database, partial homology is detected with the glycosaminoglycan binding region of human neuroglycan C (32% identity over 102 amino acids; BestFit quality=83 versus 37±5 when lacritin sequence was randomized) and with the 'cysteine-free', possibly mucin-like, amino globular region of human fibulin-2 (30% identity over 81 amino acids; BestFit quality=81 versus 38±5 for random). Although all three are rich in O-glycosylation, positioning of serine and threonine is not strictly shared; and both lacritin and fibulin-2 lack glycosaminoglycan binding sites. Neuroglycan C (af059274) is a component of brain extracellular matrix (anchored by transmembrane domain; Yasuda et al, 1998). Fibulin-2 (×89494) is widely dispersed in basement membranes and stroma of embryonic and adult tissues (Sasaki et al, 1999). Searches of non-primate databases pointed to modest homologies with T. Cruzi mucin-like protein (af036464; BestFit quality=78 versus 46±10); P. falciparum merozoite surface antigen 2 (u91656; BestFit quality=76 versus 53±6) and P. Taeda putative arabinogalactan protein (af101791; BestFit quality=74 versus 37±4).

No matching or homologous EST's were detected, in keeping with lacritin's abundance in human lacrimal gland and restricted expression elsewhere. Northern analysis revealed a strong 760 bp lacrimal gland message, and weaker submandibular and thyroid gland messages of the same size. No message was detected in human adult adrenal gland, testis, thymus, pancreas, small intestine or stomach; nor in human fetal brain lung, liver or kidney. Similarly, in a commercial dot blot of fifty different human tissue poly A+ RNA's that excluded lacrimal gland, lacritin expression was found only in submandibular gland ('salivary gland'), and to a lesser degree in thyroid. The lacritin coding sequence was subcloned into pET-28b and pcDNA3.1/myc-His(+)C to generate recombinant bacterial and mammalian (293-T cell) lacritin, respectively. Both forms of lacritin displayed anomalous migration in SDS PAGE.

EXAMPLE 2

Characterization of Lacritin Expression and Function

Preparation of Recombinant Lacritin and Anti-Lacritin Antisera

Full length lacritin cDNA was subcloned in frame into pET-28b (Novagen, Madison Wis.), with orientation confirmed by completely sequencing through the insert. Recombinant His-tagged lacritin was then generated by IPTG-induction of BL-21 transformed cells, and purified from media on Talon (Clontech; Palo Alto Calif.) resin using standard denaturing procedures. Required use of denaturing conditions for the binding step is presumed to reflect His tag inaccessibility due to folding in the absence of glycosylation. After elution, lacritin was extensively dialyzed versus PBS, and the His tag was removed by thrombin cleavage. Protein quality was assessed by SDS PAGE and Western blotting with anti-His antibody (Santa Cruz Biotechnology; Santa Cruz Calif.). Lacritin displays anomalous mobility in SDS PAGE. Lack of contaminating bacterial lipopolysaccharide was confirmed by the limulus amebocyte lysate assay (MRL Reference Lab; Cypress Calif.). For analytical comparison, small amounts of mammalian lacritin were expressed in 293T cells using pcDNA3.1/myc-His(+) (Invitrogen, Carlsbad Calif.) containing lacritin insert, and then purified under native conditions.

Anti-bacterial lacritin antiserum was subsequently prepared in rabbits (Covance Research Products, Denver Pa.), and assessed by ELISA (1/1000 dilution) using recombinant bacterial lacritin (4 µg/ml) as coat and preimmune serum (1/1000) as control. For immunohistochemistry, sections of zinc formalin-fixed, paraffin-embedded human tissues and a human tissue microarray were deparaffinized and rehydrated, and microwave heated (20 min in 10 mM citrate buffer, pH 6.0) to expose antigen. Endogenous peroxidase was blocked, and then immunodetection was performed using the avidin-biotin-peroxidase complex method (Vectastain Elite kit, Vector Laboratories, Burlingame, Calif.) after incubation with anti-lacritin antiserum or preimmune serum (1/1000) for one hour at room temperature. Sections were counterstained with hematoxylin, placed in cupric sulfate, and then immersed in lithium carbonate.

Cell Function Analysis

Freshly isolated rat lacrimal acinar cells, and HSG (human salivary gland) ductal and HCE (human corneal epithelial) cell lines were used to study lacritin function. For secretion studies, rat acinar cells were plated serum-free overnight on wells co-coated with 0.05 μM laminin 1 (to ensure adhesion) and 0 to 20 μM lacritin, or alternatively with laminin-1 (0.05 μM) and treated the next day with serum-free medium containing 0 to 162 ng/ml of soluble lacritin for four hours. Unstimulated and stimulated (carbachol 10-4 M/VIP 10-8 M) secretions were then collected, assessed (peroxidase assay) and normalized to μg cellular DNA. To study tyrosine phosphorylation, overnight serum-free cultures of both rat lacrimal acinar and HSG cells were washed and treated with 10 ng/ml of soluble lacritin for 0.5, 2.5, 10 and 30 min. Py(20) anti-phosphotyrosine antibody immunoprecipitation of cell lysates was then examined in Western blots of 7% SDS PAGE gels using Py(20) and ECL for detection. Calcium signaling in human corneal epithelial cells was similarly carried out in serum-free culture (Trinkaus-Randall et al, 2000; Klepeis & Trinkaus-Randall, in preparation). HCE cells were grown to confluency on glass coverslips in keratinocyte media (Life Technologies, Rockville Md.) containing bovine pituitary extract (30 μg/ml), EGF (0.1 ng/ml) and penicillin/streptomycin, and rendered quiescent 18 hrs before loading with Fluo-3AM (2 μM; Molecular Probes, Eugene Oreg.) at 37° C. for 30 min. Using an inverted Zeiss 510 LSM for visualization, 50 sec baseline images were first recorded. While the laser was running, lacritin was added (final concentration 4 and 40 ng/ml) and the response continually monitored every 786 msec for a minimum of 200 sec.

ECM Binding Studies

Binding studies were carried out in 96 well plates coated with 10 μg/well of collagen IV, laminin-1, entactin/nidogen-1, collagen I, fibronectin, vitronectin, EGF, heparin or BMS (Matter & Laurie, 1994). Wells were washed, blocked (PBS-T), incubated with 0-30 nM lacritin (in PBS-T containing 1% BSA) for 1 hr (4° C.), washed and detected with anti-lacritin antibody (1/1000) by ELISA.

Results:

Antibodies prepared against bacterial lacritin were applied to sections of human lacrimal and salivary glands and to tissue microarrays containing formalin-fixed, paraffin embedded sections of 75 different human tissues and organs (see Table I). Immunoreactivity was clearly observed in secretory granules of acinar cells in lacrimal and major and minor salivary glands, but was not apparent in other epithelia or stroma. Presence in thyroid was equivocal (Table I). Frequency of acinar cell staining was high in lacrimal gland, whereas only scattered salivary acinar cells were reactive. Immunoreactivity was also apparent in secretions within lumens of lacrimal and salivary ducts. By ELISA, lacritin was detected in human tears and to a lesser extent in saliva.

TABLE I

Restricted Immunolocalization of Lacritin in Human Organs[a]

| | |
|---|---|
| adrenal medulla | – |
| adrenal cortex | – |
| appendix | – |
| bladder | – |
| bone/marrow | – |
| brain | – |
| breast | – |
| bronchus | – |
| cerebellum | – |
| colon | – |
| epididymis | – |
| esophagus | – |
| gallbladder | – |
| ganglia | – |
| heart | – |
| kidney | – |
| lacrimal gland | ++++ |
| liver | – |
| lung | – |
| lymphatics | – |
| ovary | – |
| pancreas | – |
| parathyroid | – |
| parotid gland | + |
| periph. nerve | – |
| pituitary gland | – |
| placenta | – |
| prostate | – |
| testes | – |
| minor salivary | + |
| sem vesicle | – |
| skel muscle | – |
| skin | – |
| small intestine | – |
| spinal cord | – |
| spleen | – |
| stomach | – |
| subman gland | ++ |
| testis | – |
| thymus | – |
| thyroid gland | ? |
| uterus/vagina | – |

[a]relative intensity; not all tissues shown

Lacritin function was assessed in serum-free cultures of lacrimal acinar, salivary ductal and corneal epithelial cells using secretion (acinar), proliferation (ductal), tyrosine phosphorylation (acinar, ductal) and calcium signaling (corneal epithelial) assays. Freshly isolated rat lacrimal acinar cells were plated on increasing amounts of lacritin (with a constant small amount of laminin 1 to ensure adherence), or on laminin-1-coated wells in which lacritin was added to the medium. Both coated and soluble lacritin enhanced unstimulated secretion in a dose-dependent manner (see FIG. 1), but no effect was observed on the stimulated secretory pathways activated by the agonists carbachol and VIP. These results suggest an autocrine or paracrine role, possibly via receptors on the luminal acinar cell surface. As lacritin flows from acini, it contacts ductal epithelial cells and finally the corneal epithelium.

Figure 2A:
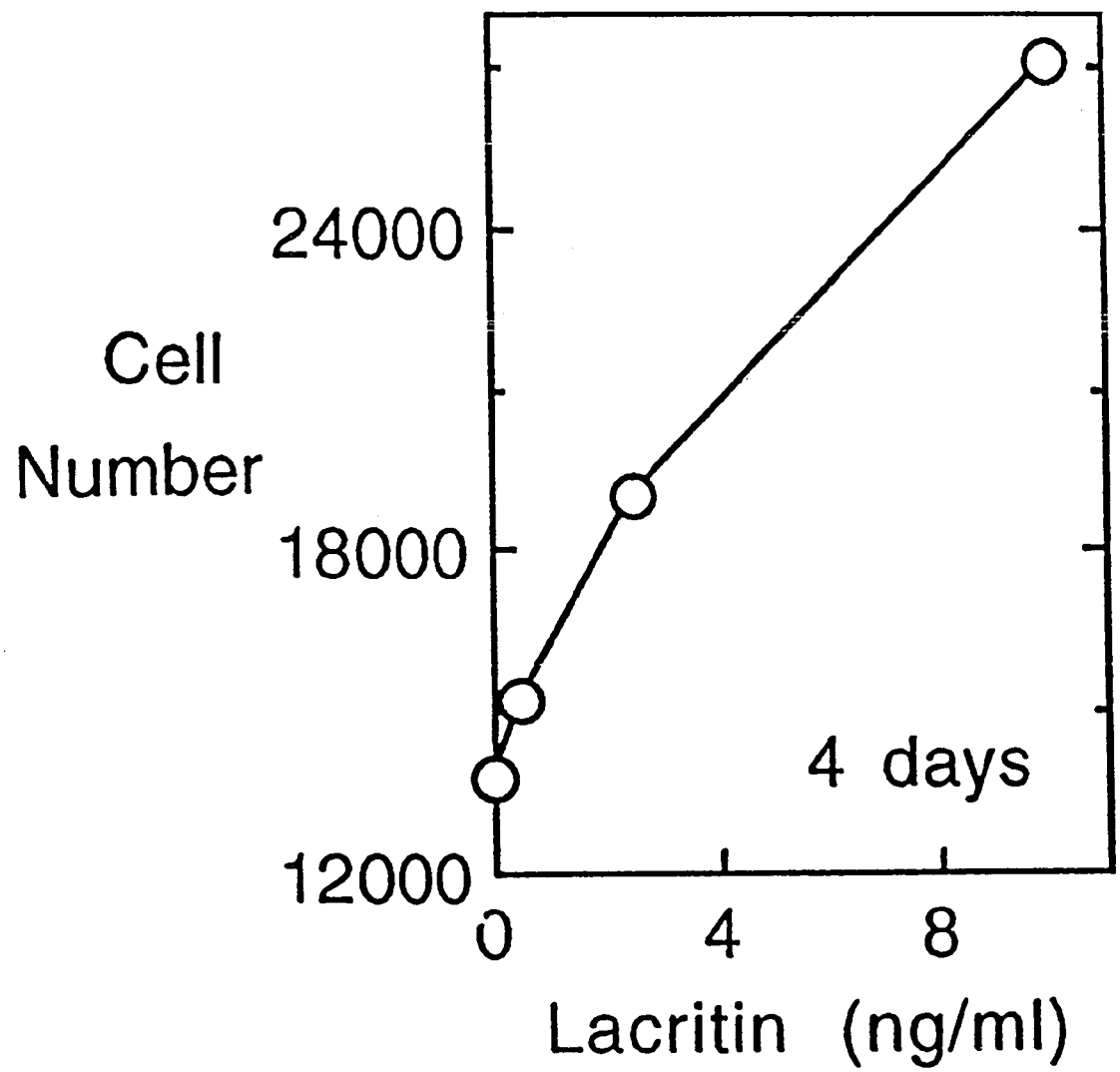
FIGS. 2A and 2B represent lacritin-induced proliferation and tyrosine phosphorylation.
Figure 2B:
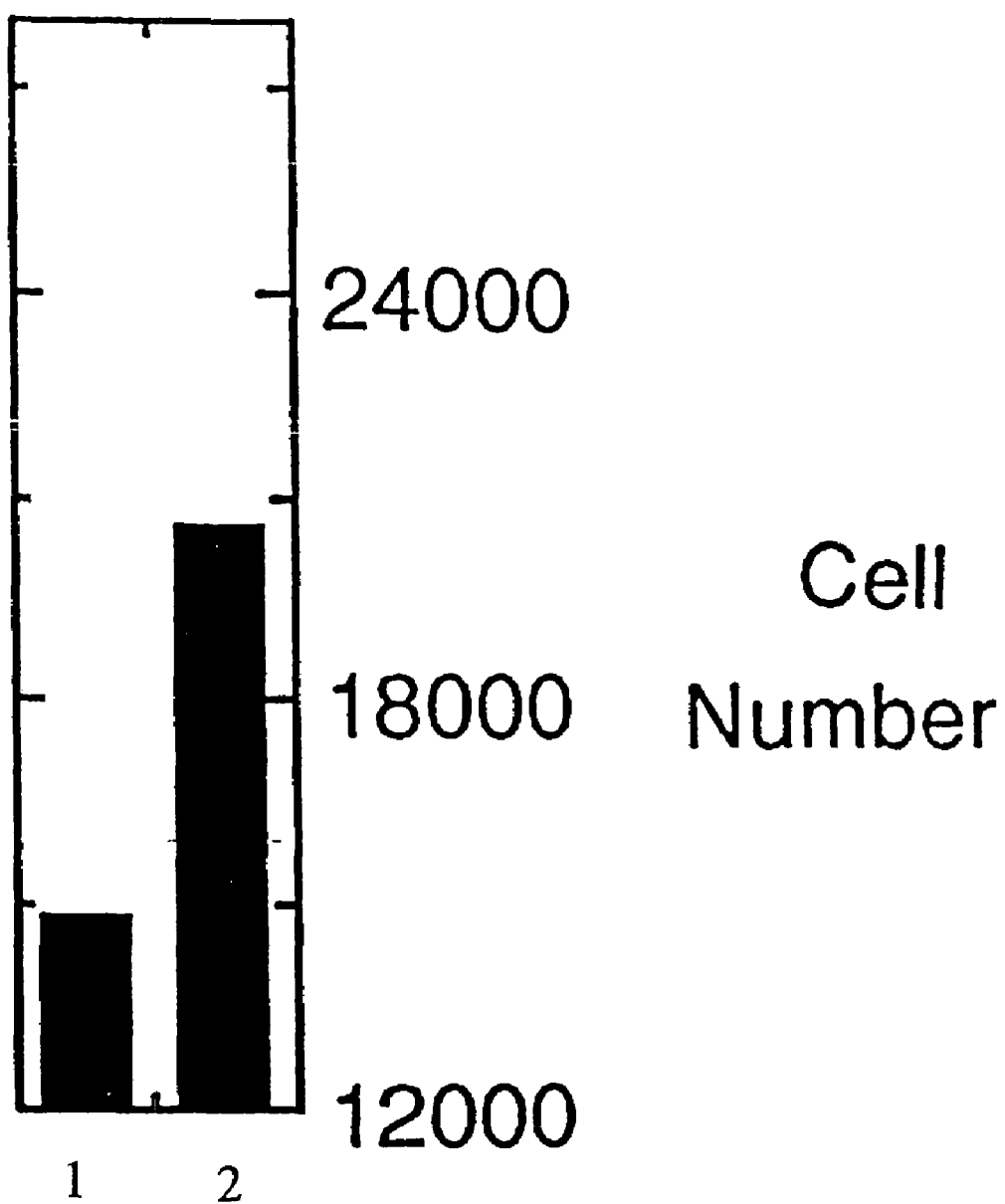

Quiescent human submandibular ductal ('HSG') cells were cultured in serum-free media containing increasing amounts of lacritin and cell proliferation was studied. The lacritin cultures looked healthier; after four days, a dose-dependent increase in ductal cell number was apparent (see FIG. 2a) that reached a level more than twofold that of the BSA (10 ng/ml) negative control (see FIG. 2b). The same level of lacritin promoted the transient tyrosine phosphorylation of a 48 kDa band in both HSG and rat lacrimal cells.

Next, calcium signals in human corneal epithelial cells were examined. Whereas the basal level of signaling was negligible, the addition of lacritin resulted in rapid and sustained calcium waves that propagated throughout the cells. Wave onset preceded that of the usual response to epidermal growth factor (20-40 sec), and the amplitude of the response depended on the concentration of lacritin. To ensure that bacterial lipopolysaccharide (a possible contaminant of recombinant protein preps) was not involved, samples were tested in the limulus amebocyte lysate assay; and no lipopolysaccharide was detected (<0.05 EU/ml). Finally, the ability of lacritin to bind the tear film components fibronectin or vitronectin was examined; as well as constituents of the periacinar basement membrane that might harbor small amounts of lacritin not detectable by the immunohistochemical procedure. Lacritin displayed a remarkable avidity for fibronectin and vitronectin, and there was a strong basement membrane binding attributable to collagen IV, nidogen/entactin and laminin-1-similar to that observed for fibulin-2 (Sasaki et al, 1995). No binding was observed to collagen I, EGF or heparin.

The rather broad lacritin lacrimal gland message was suggestive of alternatively spliced forms, or RNA degradation. The same was not true for submandibular gland in which a discrete, but much less intense signal was apparent. To address this issue and to gain information on how the lacritin gene is arranged, a 12.4 kb genomic fragment was sequenced, the largest lacritin-positive fragment readily obtainable from the lacritin genomic clones. The gene consists of five exons preceded by a predicted promoter sequence 109 to 59 bp upstream of the translation start site (promoter score=1.0; NNPP/Eukaryotic). Exon 1 encodes the complete signal peptide and includes 38 bp of 5' untranslated sequence. Exon 3 contains sequence for all putative 0-glycosylation sites. The predicted N-glycosylation site is formed at the exon 4/exon 5 splice junction. Exon 5 includes 53 bp of 3' untranslated sequence. Three potential polyadenylation sites are detected 367, 474 and 534 bp downstream of exon 5, the first of which would be in keeping with a 760 bp transcript. Sequences at exon-intron boundaries all conform to predicted splice donors or acceptors, with the exception of the exon 4 splice acceptor. Intronic sequences revealed common intronic repeat elements. Also independently discovered on a separate genomic fragment was a lacritin pseudogene lacking 38 bp of 5' exon 1 sequence.

To examine possible alternative splicing, RT-PCR was used with submandibular or lacrimal gland cDNA as template and forward and reverse primers from exons 1 and 5, respectively, each including untranslated flanking sequence. A single PCR product was detected in both organs whose size (449 bp) was in keeping with transcription from all five exons without alternative splicing. FISH revealed that the lacritin gene is located on chromosome 12, a result confirmed by double labeling with a probe for 12q15. Measurement of ten specifically labeled chromosomes located the lacritin gene approximately 16% of the distance from the centromere to the telomere of 12q, an area that corresponds to 12q13. Also found on 12q13 is a rare genetic alacrimia known as Triple A Syndrome. Attempted PCR using iacritin genomic primers and BAC templates spanning the triple A syndrome region failed to produce PCR product. The lacritin gene is partially included in draft sequences AC068789.4, AC025686.2 and AC025570.6 pointing to a 12q13 location approximately 65.1 to 65.9 Mbp from the centromere.

Discovery of lacritin developed from the hypothesis that multiple extracellular factors trigger glandular differentiation, particularly growth factors and components of the surrounding extracellular matrix. Indeed, partial or failed acinar formation has been reported in mice lacking the TGFb superfamily members or receptors, ErbB4, the progesterone receptor, the extracellular matrix glycoprotein osteopontin, EGF receptor (with TGFa and amphiregulin), fibroblast growth factor receptor 2 (IIIb), or the growth factor FGF-10. Linking such factors to the secretory function of acinar cells in culture has proven more complex. Nonetheless, it is clear that the periacinar mesenchymal and hormonal environment affect glandular development and function, and that both autocrine and paracrine regulation play important roles. Most delicate are primary cultures of freshly isolated exocrine cells, particularly lacrimal acinar cells that functionally dedifferentiate in the absence of lacrimal-1 and lower molecular mass factors derived from the extracellular matrix and elsewhere.

Introduction of recombinant lacritin to cultures of lacrimal acinar, salivary ductal and corneal epithelial cells provided interesting functional insights. Lacrimal acinar cells displayed enhanced unstimulated (but not stimulated) secretion and rapid tyrosine phosphorylation of a 48 kDa protein. Ductal cells phosphorylated the same 48 kDa band and were proliferative. A rapid and sustained calcium transient was noted in corneal epithelial cells. Thus all cell types contributing to or benefiting from lacritin outflow appear to be lacritin-inducible, whereas controls were negative and there was no evidence of contaminating bacterial lipopolysaccharide (known to be proliferative in immune cell cultures). How lacritin acts remains to be elucidated. Possibly a common receptor(s) is mediatory, ligation of which may be jointly linked to tyrosine phosphorylation and calcium release as in neural retina where tyrosine kinases have been associated with capacitative calcium entry and inositol-3-phosphate induced release of intracellular calcium stores. Alternatively, lacritin signaling in the three cell types may differ. Lacrimal acinar, ductal and corneal epithelial cells perform strikingly different functions. Although some intracellular signaling machinery may be common, others are unique, and some common machinery may be put to different use. Calcium signaling in lacrimal acinar cells is most frequently a downstream effect of muscarinic receptor ligation that mediates the release of tear proteins by the stimulated secretory pathway, a pathway apparently unaffected by lacritin. Yet, subtleties in calcium amplitude, frequency and localization, dependent on the nature and dose of the agonist, can have dramatically different effects. Contrasting lacritin is BM180, a periacinar basement membrane constituent that appears to act only on the stimulated secretory pathway. Balancing the amounts of available lacritin and BM180 may offer a simple mechanism by which secretory capacity in adult and developing glands may be controlled.

Immunolocalization of lacritin in secretory granules, in secretory content of ducts and in tears was extended by binding studies revealing a remarkable affinity for tear constituents fibronectin and vitronectin. Though not immunodetected elsewhere, lacritin also bound the common periacinar basement membrane components nidogen/entactin, collagen IV, and laminin-1; but not collagen I, EGF or heparin. Similar binding properties have been reported for fibulin-2 (Sasaki et al, 1995). Although the significance and precise nature of these interactions remains to be determined, basement membrane binding is perhaps analogous to growth factors whose extracellular matrix accumulation, although functionally potent, is often too low for reliable immunodetection. Alternatively, basement membrane binding (if any) could possibly occur secondary to tissue damage.

EXAMPLE 3

Characterization of the Lacritin Promoter

The working hypothesis is that lacritin gene activity is attributable to an atypically restrictive and powerful promoter working hand in hand with unique enhancer (and possibly repressor) elements in a milieu of appropriate transcription factors and co-regulators. Such tissue-specific transcriptional control equals or exceeds that of the aA-crystallin (lens), rhodopsin (retina), aldehyde dehydrogenase class 3 and keratocan genes (cornea), and offers a unique opportunity to initiate a new body of literature on nuclear management of gene expression in the human lacrimal gland.

Mapping of Lacritin Gene Regulatory Elements

Elucidating how lacritin gene expression is targeted to the lacrimal gland will be determined as described below to better understanding lacrimal gene regulation. First of all the identify the lacritin transcription initiation site(s) will be confirmed experimentally. Based on computational promoter analysis, transcription is anticipated to be initiated at a single site located 69 bp upstream ('−69 bp'; 'Neural Network') of the ATG translation start site. The 'TATA-box' and/or 'Initiator' ('Inr') elements of the core promoter play an important role in establishing the start site of transcription in many genes, particularly those highly expressed. As an example, Inr elements at +1, +220 (also TATA-box at +190 bp) and +316 bp (intronic) designate transcription start sites in the human keratocan gene as experimentally confirmed by primer extension (see Tasheva E S, Conrad A H, Conrad G W. Identification and characterization of conserved cis-regulatory elements in the human keratocan gene promoter. Biochim Biophys Acta. 2000 Jul 24;1492(2-3):452-9); and a TATA-box figures prominently in transcription initiation of aA crystallin, rhodopsin, and aldehyde dehydrogenase gene promoters. If the Neural Network-predicted −94 to −46 bp region does indeed comprise the lacritin core promoter with transcription start site at −69 bp (score=1.0), then putative TATA-box and Inr elements at −52 and −67 bp, respectively should play a key role in transcription initiation. Alternatively, transcription could begin at −62 bp, as suggested by 'CorePromoter'. Primer extension and RNA ligase-mediated 5'-RACE will resolve this question.

For primer extension, advantage will be taken of a 20-mer reverse primer ('LacP83') designed by 'Prime' (GCG, Madison Wis.) which is complementary to nucleotides 64 to 83 bp of lacritin mRNA. As per routine procedure, LacP83 will be end-labeled by phosphorylation with T4 polynucleotide kinase in the presence of $[g^{32}P]ATP$, annealed with total lacrimal RNA (100 fmol primer per 10 µg RNA) for 20 min at 58° C., cooled, and then incubated for 30 min at 41° C. with AMV reverse transcriptase (Promega, Madison Wis.) in the presence of deoxynucleotides. Size of newly formed cDNA(s), as analyzed by denaturing SDS PAGE analysis/radiography, provides sufficient information to calculate the approximate transcription start site location(s)—with identification of the 5' terminus(i) determined by semi-automatic ABI sequencing of cDNA from a scaled up non-radioactive extension reaction and RNA ligase-mediated 5'-RACE. Primer extension controls will include replacement of lacrimal RNA with total yeast RNA (or no RNA), and use of an RNA prepared by in vitro transcription with accompanying primer (Promega, Madison Wis.) for which primer extension conditions have been previously established.

For confirmation, RNA ligase-mediated 5'-RACE ('GeneRacer'; Invitrogen) will be utilized. This is a powerful PCR-based modification of primer extension. For this purpose, 1-5 µg of total human lacrimal RNA will be treated with calf intestinal phosphatase (1 U per 10 µl reaction mix) to remove 5' phosphates from degraded RNA and non-mRNA contaminants. Incubation with tobacco acid pyrophosphatase (0.5-1 U per 10 µl reaction mix) eliminates the 5'-CAP structure present only on authentic 5'-ends, and makes possible ligation of a kit-specific RNA oligonucleotide ('GeneRacer RNA Oligo') with T4 RNA ligase (5 U per 10 µl reaction mix). Subsequent LacP83-primed reverse transcription will generate a single strand cDNA. The cDNA will then be PCR amplified using LacP83 and a primer complementary to the 5' RNA oligo as primer pair, and sequenced to identify the start site(s). In negative PCR controls, amplifications will be attempted in the absence of LacP83 or GeneRacer RNA Oligo or without template, and if banding or smearing is observed further PCR optimization will be carried out (ie. use of less template or fewer PCR cycles or do nested PCR to increase amplicon amount, or use touchdown PCR).

It is anticipated that a single primer extended cDNA band of 152 (or 145) bp will be observed in keeping with a transcription start site at −69 bp (or −62 bp) and inclusion of 83 bp from the 5' end of the primer to the translation start site [69+83 bp (or 62+83 bp)]. This expectation is in agreement with the single transcript apparent by Northern analysis of human salivary gland. The broader human lacrimal band has been interpreted as attributable to MRNA abundance combined with possibly some slight degradation. Although no alternative splicing has been observed, the possibility of a second transcript cannot be completely ruled out.

A luciferase reporter constructs will also be generated and transfection-based regional mapping of lacritin gene regulatory elements will be initiated. It is hypothesized that Bayesian alignment of human and mouse lacritin genes will provide an excellent foundation for interpretation of reporter construct activity, and that evolutionary conservation similarly will make feasible utilization of a rabbit lacrimal acinar cell line as transfection host—the only immortalized cell line from lacrimal gland of any species. This exploratory approach will lay the conceptual groundwork for more detailed studies both in vitro and in vivo.

Lacritin's tissue specificity is presumably founded in the nature and assortment of transcription factor binding modules that comprise its gene promoter and putative enhancer region(s). Lens-preferred expression of the aA-crystallin gene, for example, is governed by a transcription complex of CREB/CREM, aA-CRYBP1, Pax 6, TBP, USF, AP-1 (context of AP-1 important for tissue specificity) and L-maf that nucleates on the 150 bp aA-crystallin promoter. Transfected plasmid constructs that artificially position luciferase or chloramphenicol acetyltransferase expression under the control of intact or progressively 5' shortened (or mutated) promoter regions, has been used previously to identify cis-acting regulatory region of a promoter. The versatile and sensitive 'Dual-Luciferase Reporter Assay System' (Promega) for example sequentially assays both the transfected gene promoter under investigation (as manifested by the level of expressed firefly luciferase) and a co-transfected internal positive HSV-TK control promoter designed to independently drive expression of a synthetic sea pansy luciferase with distinct substrate properties at a constant baseline level (see below). Subsequent investigation in transgenic mice using b-galactosidase as reporter brings chromosomal context into play. Recent availability of a rabbit lacrimal cell line (Nguyen D H, Beuerman R W, Halbert C L, M a Q, Sun G. Characterization of immortalized rabbit lacrimal gland epithelial cells. In Vitro Cell Dev Biol Anim. 1999 April; 35(4):198-204.) and genomic cloning of lacritin now open up this line of investigation to the lacrimal gland field.

If transcription is indeed initiated at −69 or −62 bp, upstream genomic constructs spanning −2435 to −10 bp ('Lacrgen2.4'), −1619 to −10 bp ('Lacrgen1.6') or −856 to −10 bp ('Lacrgen0.9') could include all or most elements necessary for tissue specific and elevated expression. Preparation of each will take advantage of parent amplicon 'LacrgenInit' (−2960 to −10 bp) to be generated by PCR from the 12.4 kb lacritin genomic fragment using reverse primer 'LacP-10/Xho I' (−10 to −31 bp) with an Xho I site incorporated, and forward primer 'LacP-2960' (−2960 to −2942 bp). Primer pairs are designed by 'Prime' (GCG, Madison Wis.). Subsequent digestion of LacrgenInit with XhoI, Bgl II/Xho I or Hind III/Xho I yields fragments Lacrgen2.4, Lacrgen1.6 or Lacrgen0.9, respectively with ends suitable for ready ligation (after gel purification) into the multiple cloning region of pGL3-Basic just upstream of the promoterless and enhancerless luciferase gene (luc+).

A new rabbit lacrimal acinar cell line (Nguyen et al, '99), that has been cultured for twelve months without difficulty will be used for the transfection studies. The cells display a strong epithelial morphology and synthesize secretory component, transferrin and transferrin receptor. Importantly, they also express lacritin and are readily transfectable. To carry out transfections, ≈80% confluent serum-containing cultures in 96 well plates will be transiently transfected with Lacrgen2.4, Lacrgen1.6 or Lacrgen0.9 in pGL3-Basic plus internal control phRL-TK plasmid (total of 0.24 µg plasmid/well; 50:1 ratio of pGL3-Basic to phRL-TK) using ≈0.8 µl/well LipofectAMINE 2000 reagent (Invitrogen Life Technologies). 48 hours later, cultures will be gently washed three times in PBS, lysed for 15 min in 1X 'Passive Lysis Buffer' (20 µl/well; Promega), and assayed for firefly luciferase upon addition of 'Luciferase Assay Reagent II' (100 µl/well) in an L-Max 96 well plate luminometer (Molecular Devices, Menlo Calif.; online with computer). Readings are zeroed to similarly treated wells containing lysate of cells not transfected. Subsequently, 'Stop & Glo Reagent' (100 µl/well) is added for assay of sea pansy (Renilla) luciferase. Inclusion of identically transfected human 293 cells will serve as a negative control, whereas Araki-Sasaki human corneal epithelial cells (HCE-T) and HSG human salivary cells (both secrete lacritin) are suitable positive controls. Optimal lacrimal LipofectAMINE transfection, and 'Bright-Glo' luciferase assay conditions (Promega), will take advantage of the pGL3-Control vector whereby transfected cells benefit from luc+ expression under SV40 promoter and enhancer control. It is expected that transfection efficiency will be 75-90%, and that one of Lacrgen2.4, Lacrgen1.6 or Lacrgen0.9—likely Lacrgen1.6 or Lacrgen0.9—will best define the minimal sequence required for lacritin promoter activity.

This course of investigation offers a logical starting point for the generation and testing of Lacrgen2.4, Lacrgen1.6 or Lacrgen0.9-derived constructs progressively shortened 5' by nested deletion, an approach applied to the genomic sequencing of the lacritin gene and flanking regions. Making this possible are single Kpn I and Sac I sites just upstream of each insert in the pGL3-Basic multiple cloning region, and lack of any internal Kpn I or Sac I sites in Lacrgen2.4, Lacrgen1.6 or Lacrgen0.9—the latter as determined by Map (GCG). Thus when digested with Kpn I and Sac I, a linear plasmid will be generated in which the Kpn I end is exonuclease III resistant (3' protruding) and the Sac I end (3' recessed) is sensitive. Proximity of Lacrgen2.4, Lacrgen1.6 or Lacrgen0.9 to the Sac I site makes them sensitive to exonuclease shortening. To carry this out, 2 µg of plasmid construct is Kpn I and Sac I digested. After enzyme inactivation (10 min at 70° C.) and cooling on ice, linear plasmid in exonuclease III buffer is treated with exonuclease III in a final volume of 40 µl at 25° C. or 15° C. such as to achieve successive 50-100 bp deletions at 3 min intervals. 2 µl aliquots of each 3 min time point are removed to tubes on ice containing S1 nuclease. After all timed aliquots have been taken, plasmid digests are removed from ice, incubated at room temperature for 30 min for S1 nuclease digestion of overhangs, heat inactivated, recirculized by blunt end ligation in the presence of T4 DNA ligase, examined in agarose gels and transformed into competent cells with ampicillin selection. Plasmid preps of each are then applied to the transfection (with internal control plasmid) of lacrimal acinar cells, and assessment of luciferase expression.

The invention claimed is:

1. A method for identifying a nucleic acid sequence encoding a lacritin receptor, said method comprising providing cells that have been transfected with nucleic acid sequences that encode for potential cell receptors;

contacting said transfected cells with lacritin (SEQ ID NO:4);

detecting cells that display lacritin-dependent calcium signaling;

isolating nucleic acid sequences from the detected cells; and identifying a nucleic acid sequence that confers lacritin-dependent calcium signaling on cells transfected with that nucleic acid sequence.

* * * * *